US009987299B2

United States Patent

(12) United States Patent
McCray, Jr. et al.

(10) Patent No.: US 9,987,299 B2
(45) Date of Patent: Jun. 5, 2018

(54) METHODS OF IMPROVING RNAI IN WELL-DIFFERENTIATED AIRWAY EPITHELIA

(71) Applicant: University of Iowa Research Foundation, Iowa City, IA (US)

(72) Inventors: Paul B. McCray, Jr., Iowa City, IA (US); Beverly L. Davidson, Iowa City, IA (US); Michael A. Apicella, Iowa City, IA (US); Sateesh Krishnamurthy, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days. days.

(21) Appl. No.: 14/703,536

(22) Filed: May 4, 2015

(65) Prior Publication Data

US 2015/0313924 A1 Nov. 5, 2015

Related U.S. Application Data

(60) Provisional application No. 61/988,742, filed on May 5, 2014, provisional application No. 62/000,352, filed on May 19, 2014.

(51) Int. Cl.

| | |
|---|---|
| ***A61K 31/713*** | (2006.01) |
| ***A61K 31/685*** | (2006.01) |
| ***A61K 31/715*** | (2006.01) |
| ***A61K 45/06*** | (2006.01) |
| ***A61K 31/7024*** | (2006.01) |
| ***A61K 31/7032*** | (2006.01) |

(52) U.S. Cl.

CPC .......... *A61K 31/713* (2013.01); *A61K 31/685* (2013.01); *A61K 31/7024* (2013.01); *A61K 31/7032* (2013.01); *A61K 31/715* (2013.01); *A61K 45/06* (2013.01)

(58) Field of Classification Search

CPC .................................................... A61K 48/00

See application file for complete search history.

(56) References Cited

U.S. PATENT DOCUMENTS

| | | | |
|---|---|---|---|
| 4,559,157 | A | 12/1985 | Smith |
| 4,608,392 | A | 8/1986 | Jacquet |
| 4,820,508 | A | 4/1989 | Wortzman |
| 4,938,949 | A | 7/1990 | Borch et al. |
| 4,992,478 | A | 2/1991 | Geria |
| 6,855,549 | B1 | 2/2005 | McCray, Jr. et al. |
| 8,084,599 | B2 | 12/2011 | Rossi et al. |

OTHER PUBLICATIONS

Watarai, et al., "Legionella pneumophila is internalized by a macropinocytotic uptake pathway controlled by the Dot/Icm system and the mouse Lgn1 locus", J Exp Med 194 (8), 1081-1096 (2001).

Watts, et al., "Endocytosis: what goes in and how?", J Cell Sci 103 (Pt 1): 1-8 (1992).

Xu, et al., "Disruption of the F-actin cytoskeleton and monolayer barrier integrity induced by PAF and the protective effect of ITF on intestinal epithelium", Arch Pharm res 34 (2), 245-251 (2011).

Yamaya, et al., "Differentiated structure and function of cultures from human tracheal epithelium", Am J Physiol 262 (6 Pt 1): L713-724 (1992).

Zhang, et al., "Inhibition of respiratory syncytial virus infection with intranasal siRNA nanoparticles targeting the viral NS1 gene", Nat Med 11 (1), 56-62 (2005).

Zhang, et al., "Small interfering RNA targeting heme oxygenase-1 enhances ischemia-reperfusion-induced lung apoptosis", J. Biol Chem 279 (11), 10677-10684 (2004).

Zhang, et al., "The polymeric immunoglobulin receptor translocates pneumococci across human nasopharyngeal epithelial cells", Cell 102 (6), 827-837 (2000).

Zuhorn, et al., "Gene delivery by cationic lipid vectors: overcoming cellular barriers", Eur Biophys J. 36 (4-5) 349-362 (2007).

Alvarez, et al., "RNA interference-mediated silencing of the respiratory syncytial virus nucleocapsid defines a potent antiviral strategy", Antimicrob Agents Chemother 53 (9), 3952-3962 (2009).

Amarzguioui, et al., "Rational design and in vitro and in vivo delivery of Dicer substrate siRNA", Nat Protoc 1 (2), 508-517 (2006).

Bitko, et al., "Inhibition of respiratory viruses by nasally administered siRNA", Nat Med 11 (1), 50-55 (2005).

Bussolino, et al., "Human endothelial cells are target for platelet-activating factor. I. Platelet-activating factor induces changes in cytoskeleton structures", J Immunol 139 (7), 2439-2446 (1987).

Chao, "Platelet-activating factor: receptors and signal transduction", Biochem J 292 (Pt 3): 617-629 (1993).

Collingwood, et al., "Chemical modification patterns compatible with high potency dicer-substrate small interfering RNAs", Oligonucleotides 18 (2), 187-200 (2008).

Cundell, et al., "*Streptococcus pneumoniae* anchor to activated human cells by the receptor for platelet-activating factor", Nature 377, 435-438 (1995).

Davidson, et al., "Current prospects for RNA interference-based therapies", Nat Rev Genet 12 (5). 329-340 (2011).

Devincenzo, et al., "A randomized, double-blind, placebo-controlled study of an RNAi-based therapy directed against respiratory syncytial virus", Proc Natl Acad Sci 107 (19), 8800-8805 (2010).

Eguchi, et al., "Efficient siRNA delivery into primary cells by a peptide transduction domain-dsRNA binding domain fusion protein", Nat Biotechnol 27 (6), 567-671 (2009).

Francis, et al., "Ruffles induced by *Salmonella* and other stimuli direct macropinocytosis of bacteria", Nature 364 (6438), 639-642 (1993).

Ge, et al., "Inhibition of influenza virus production in virus-infected mice by RNA interference", Proc Natl Acad Sci 101 (23), 8676-8681 (2004).

(Continued)

*Primary Examiner* — Kimberly Chong

(74) *Attorney, Agent, or Firm* — Viksnins Harris Padys Malen LLP

(57) ABSTRACT

The present invention relates to methods of reducing a level of a target mRNA in a well-differentiated airway epithelial cell by contacting the cell with a facilitating agent followed by contacting the cell with a therapeutic RNAi agent, wherein the facilitating agent comprises a Platelet-activating factor receptor (PAFR) ligand.

13 Claims, 9 Drawing Sheets

(56) References Cited

OTHER PUBLICATIONS

Goel, et al., "Phorbol esters: structure, biological activity, and toxicity in animals", Int J Toxicol 26 (4), 279-28 (2007).
Henson, et al., "NHLBI workshop summary. Platelet-activating factor: role in pulmonary injury and dysfunction and blood abnormalities", Am Rev Respir Dis 145 (3), 726-731 (1992).
Imamura, et al., "Single particle tracking confirms that multivalent Tat protein transduction domain-induced heparan sulfate proteoglycan cross-linkage activates Rac1 for internalization", J Biol Chem 286 (12), 10581-10592 (2011).
Judge, et al., "Sequence-dependent stimulation of the mammalian innate immune response by synthetic siRNA", Nat Biotechnol 23 (4), 457-462 (2005).
Kaplan, et al., "Cationic TAT peptide transduction domain enters cells by macropinocytosis", J Control Release 102 (1), 247-253 (2005).
Ketterer, et al., "Infection of primary human bronchial epithelial cells by Haemophilus influenzae: macropinocytosis as a mechanism of airway epithelial cell entry", Infect Immun 67 (8), 4161-4170 (1999).
Kim, et al., "Blockade of the Wnt/β-catenin pathway attenuates bleomycin-induced pulmonary fibrosis", Tohoku J Exp Med 223 (1), 45-54 (2011).
Kim, et al., "Synthetic dsRNA Dicer substrates enhance RNAi potency and efficacy", Nat Biotechnol 23 (2), 222-226 (2005).
Kleinman, et al., "Sequence- and target-independent angiogenesis suppression by siRNA via TLR3", Nature 452 (7187), 591-597 (2008).
Knezevic II, et al., "Tiam1 and Rac1 are required for platelet-activating factor-induced endothelial junctional disassembly and increase in vascular permeability", J Biol Chem 284 (8), 5381-5394 (2009).
Krishnamurthy, et al., "Manipulation of Cell Physiology Enables Gene Silencing in Well-differentiated Airway Epithelia", Mol Ther Nucleic Acids 1, e41 (2012).
Krishnamurthy, et al., "Platelet Activating Factor Receptor Activation Improves siRNA Uptake and RNAi Responses in Well-differentiated Airway Epithelia", Mol Ther Nucleic Acids 3 (7), e175, 9 pp. (2014).
Lamb, et al., "The Connectivity Map: using gene-expression signatures to connect small molecules, genes, and disease", Science 313 (5795), 1929-1935 (2006).
Lee, et al., "Mutation of the htrB locus of Haemophilus influenzae nontypable strain 2019 is associated with modifications of lipid A and phosphorylation of the lipo-oligosaccharide", J Biol Chem 270 (45), 27151-27159 (1995).
Liang et al., "Spiperone, identified through compound screening, activates calcium-dependent chloride secretion in the airway", Am J Physiol Cell Physiol 296 (1), C131-C141 (2009).
Lomas-Neira, et al., "In vivo gene silencing (with siRNA) of pulmonary expression of MIP-2 versus KC results in divergent effects on hemorrhage-induced, neutrophil-mediated septic acute lung injury", J Leukov Biol 77 (6), 846-853 (2005).
McLendon, et al., "Identification of LpxL, a late acyltransferase of Francisella tularensis", Infect Immun 75 (1), 558-5531 (2007).
Mercer, et al., "Virus entry by macropinocytosis", Nat Cell biol 11 (5), 510-520 (2009).
Merkel, et al., "Pulmonary gene delivery using polymeric nonviral vectors", Bioconjug Chem 23 (1), 3-20 (2012).
Moniot, et al., "The PGD2 pathway, independently of FGF9, amplifies SOX9 activity in Sertoli cells during male sexual differentiation", Development 136 (11), 1813-1821 (2009).
Moschos, et al., "Uptake, efficacy, and systemic distribution of naked, inhaled short interfering RNA (siRNA) and locked nucleic acid (LNA) antisense", Mol Ther 19 (12), 2163-2168 (2011).
Oakland, et al., "Advances in cell and gene-based therapies for cystic fibrosis lung disease", Mol Ther 20 (6), 1108-1115 (2012).
Perl, et al., "Silencing of Fas, but not caspase-8, in lung epithelial cells ameliorates pulmonary apoptosis, inflammation, and neutrophil influx after hemorrhagic shock and sepsis", Am J Pathol 167 (6), 1545-1559 (2005).
Pezzulo, et al., "The polymeric immunoglobulin receptor translocates pneumococci across human nasopharyngeal epithelial cells", Am J Physiol Lung Cell Mol Physiol 300 (1), L25-31 (2011).
Platz, et al., "Application of small interfering RNA (siRNA) for modulation of airway epithelial gene expression", Oligonucleotides 15 (2), 132-138 (2005).
Preston, et al., "The lipooligosaccharides of pathogenic gram-negative bacteria", Crit Rev Microbiol 22 (3), 139-180 (1996).
Robbins, et al., "A Mutator transposon insertion is associated with ectopic expression of a tandemly repeated multicopy Myb gene pericarp color1 of maize", Genetics 178 (4), 1859-1874 (2008).
Robbins, et al., "Misinterpreting the therapeutic effects of small interfering RNA caused by immune stimulation", Hum Gene Ther 19 (10), 991-999 (2008).
Rosas-Taraco, et al., "Intrapulmonary delivery of XCL1-targeting small interfering RNA in mice chronically infected with Mycobacterium tuberculosis", Am J Respir Cell Mol Biol 41 (2), 136-145 (2009).
Rose, et al., "Functional polarity is introduced by Dicer processing of short substrate RNAs", Nucleic Acids Res 33 (13), 4140-4156 (2005).
Sanders, et al., "Extracellular barriers in respiratory gene therapy", Adv Drug Deliv Rev 61 (2), 115-127 (2009).
Senoo, et al., "Suppression of plasminogen activator inhibitor-1 by RNA interference attenuates pulmonary fibrosis", Thorax 65 (4), 334-340 (2010).
Shirasak, et al., "Expression of platelet-activating factor receptor mRNA in human and guinea pig lung", Am J Respir cell Mol Biol 10 (5), 533-537 (1994).
Shukla, et al., "Platelet-activating factor receptor and signal transduction mechanisms", FASEB J 6 (6), 2296-2301 (1992).
Sinn, et al., "Viscoelastic gel formulations enhance airway epithelial gene transfer with viral vectors", Am J Respir Cell Mol Biol 32 (5), 404-410 (2005).
Stoll, et al., "Platelet-activating factor may stimulate both receptor-dependent and receptor-independent increases in [Ca2+] in human airway epithelial cells", J Biol Chem 269 (6), 4254-4259 (1994).
Swords, et al., "Non-typeable Haemophilus influenzae adhere to and invade human bronchial epithelial cells via an interaction of lipooligosaccharide with the PAF receptor", Mol Microbiol 37 (1), 13-27 (2000).
Travers, et al., "Augmentation of UVB radiation-mediated early gene expression by the epidermal platelet-activating factor receptor", J Invest Dermatol 128 (2), 455-460 (2008).

a b c

METHODS OF IMPROVING RNAI IN WELL-DIFFERENTIATED AIRWAY EPITHELIA

RELATED APPLICATION

This application claims priority to U.S. Provisional Patent Application No. 61/988,742, filed May 5, 2014, and U.S. Provisional Patent Application No. 62/000,352, filed May 19, 2014, the entirety of which are incorporated herein by reference.

GOVERNMENT FUNDING

This invention was made with government support under HL051670 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 1, 2015, is named 17023.144US1_SL.txt and is 5,141 bytes in size.

BACKGROUND OF THE INVENTION

The pulmonary airway comprises those parts of the respiratory system through which air flows, conceptually beginning (on inhalation from the external environment) at the nose and mouth, and terminating in the alveoli. From the mouth or nose, inhaled air passes through the pharynx into the trachea, where it separates into the left and right main bronchi at the carina, situated at the level of the second thoracic vertebra. The main bronchi then branch into large bronchioles, one for each lobe of the lung. Within the lobes, the bronchioles further subdivide some twenty times, ending in clusters of alveoli.

The epithelial surfaces of the airway contain cilia. Inhaled particles adhere to mucus secreted by goblet cells, which is continuously driven outwards by the cilia. The epithelium of the airway also secretes a watery fluid upon which the mucus can ride freely. The production of this fluid is impaired by the disease cystic fibrosis. Macrophages in the airways help promote prophylaxis and prevent infection and contamination, by engulfing bacteria and other inhaled particles.

Disease conditions associated with the airway include cystic fibrosis, allergies, asthma, Chronic Obstructive Pulmonary Disease (COPD) and bronchitis. Cystic fibrosis (also known as CF or mucoviscidosis) is a common recessive genetic disease which affects the entire body, causing progressive disability and often early death. The name cystic fibrosis refers to the characteristic scarring (fibrosis) and cyst formation within the pancreas, first recognized in the 1930s. Difficulty breathing is the most serious symptom and results from frequent lung infections that are treated with, though not cured by, antibiotics and other medications. A multitude of other symptoms, including sinus infections, poor growth, diarrhea, and infertility result from the effects of CF on other parts of the body.

Currently, there are no cures for cystic fibrosis, although there are several treatment methods. The management of cystic fibrosis has improved significantly over the years. While infants born with cystic fibrosis 70 years ago would have been unlikely to live beyond their first year, infants today are likely to live well into adulthood. The cornerstones of management are proactive treatment of airway infection and inflammation, and encouragement of good nutrition and an active lifestyle. Management of cystic fibrosis is aimed at maximizing organ function, and therefore quality of life. At best, current treatments delay the decline in organ function. Targets for therapy are the lungs, gastrointestinal tract (including pancreatic enzyme supplements), the reproductive organs (including assisted reproductive technology (ART)) and psychological support.

The most consistent aspect of therapy in cystic fibrosis is limiting and treating the lung damage caused by thick mucus and infection, with the goal of maintaining quality of life. Intravenous, inhaled, and oral antibiotics are used to treat chronic and acute infections. Mechanical devices and inhalation medications are used to alter and clear the thickened mucus. These therapies, while effective, can be extremely time-consuming for the patient. One of the most important battles that CF patients face is finding the time to comply with prescribed treatments while balancing a normal life.

Small-interfering RNA (siRNA)-mediated silencing of genes offers a novel approach for disease treatment. Direct delivery of siRNA to respiratory epithelia is potentially advantageous for many respiratory infections and for chronic diseases like cystic fibrosis where airway epithelial cells are prominent sites of production and release of pro-inflammatory cytokines such as IL-8 and others (Davidson B L, McCray P B, Jr. Current prospects for RNA interference-based therapies. *Nat Rev Genet* 2011; 12(5):329-340). Topical delivery avoids hepatic clearance and non-specific accumulation associated with the systemic route and allows for local accumulation within the target organ. But due to its high molecular weight and polyanionic nature, siRNAs do not cross the epithelial cell membrane freely. In addition, the intra pulmonary physical barriers such as mucus to overcome before encountering the problems with cell entry (Oakland M, Sinn P L, McCray P B Jr. Advances in cell and gene-based therapies for cystic fibrosis lung disease. Mol Ther. 2012 Feb. 28. doi: 10.1038/mt.2012.32. [Epub ahead of print] PMID: 22371844). Thus, efficient delivery of siRNA to the airways has been challenging due to significant intracellular and extracellular barriers.

Non-viral siRNA delivery is an attractive and potentially safer alternative to virus-based delivery systems. A number of studies report successful delivery of naked siRNA to airways, especially for counteracting viral infections (Zhang W et al., Inhibition of respiratory syncytial virus infection with intranasal siRNA nanoparticles targeting the viral NS1 gene. *Nat Med* 2005; 11(1):56-62; Bitko V et al., Inhibition of respiratory viruses by nasally administered siRNA. *Nat Med* 2005; 11(1):50-55). However, recent reports also show that siRNAs delivered intranasally or intratracheally, without delivery enhancement, may not target to lung cells and thus do not cause RNA interference (Moschos S A et al., Uptake, efficacy, and systemic distribution of naked, inhaled short interfering RNA (siRNA) and locked nucleic acid (LNA) antisense. *Mol Ther* 2011; 19(12):2163-2168). Furthermore, off target immunostimulatory effects of early siRNA constructs likely clouded some studies (Judge A D et al., Sequence-dependent stimulation of the mammalian innate immune response by synthetic siRNA. *Nat Biotechnol* 2005; 23(4):457-462; DeVincenzo J et al., A randomized, double-blind, placebo-controlled study of an RNAi-based therapy directed against respiratory syncytial virus. *Proc Natl Acad Sci USA* 2010; 107(19):8800-8805; Kleinman M E et al., Sequence- and target-independent angiogenesis suppression by siRNA via TLR3. *Nature* 2008; 452 (7187):591-597). Added to these disappointing results, the delivery and efficacy of siRNA in combination with various non-viral reagents in respiratory epithelia has not been extensively investigated.

Accordingly, a more effective, simple-to-administer, and efficient treatments for CF and other airway diseases are needed.

SUMMARY OF THE INVENTION

In certain embodiments, the present invention provides a method of reducing a level of a target mRNA in a well-differentiated airway epithelial cell comprising contacting the cell with a facilitating agent and a therapeutic RNAi agent, wherein the mRNA level of the target mRNA is reduced by at least 1% as compared to a control cell that has not been contacted with the facilitating compound, wherein the facilitating agent comprises a Platelet-activating factor receptor (PAFR) ligand. In certain embodiments, the PAFR ligand is Platelet-activating factor receptor (PAF), lipooligosaccharide (LOS) and/or teichoic acid. In certain embodiments, the LOS is non-typeable *Haemophilus influenzae* (NTHi) LOS. As used herein, the term "well-differentiated" cells have fully differentiated and form a pseudostratified epithelium with the diversity of cells represented in the human conducting airways (ciliated cells, goblet cells, non-ciliated cells, basal cells) and "poorly-differentiated" cells to signify cells that have not reached this differentiated state of maturation and do not form an epithelium representative of the in vivo airways. As used herein an "RNAi molecule" is an RNA molecule that functions in RNA interference (e.g., siRNA, shRNA or DsiRNA). In certain embodiments, the mRNA level is reduced by at least about 1%, 5%, 10%, 20, 30%, 40%, 50%, 60%, 70%, 80%, 90% 95%, or 99%. In certain embodiments, the well differentiated cells are more than five days old. In certain embodiments, the cell is contacted on its mucosal surface. In certain embodiments, the airway epithelial cell is a lung cell, a nasal cell, a tracheal cell, a bronchial cell, a bronchiolar or alveolar epithelial cell. In certain embodiments, the airway epithelial cells are present in a mammal. In certain embodiments, the cell is a CF epithelial cell.

In certain embodiments, the RNAi molecule is an siRNA, an miRNA, a microRNA mimic, and anti-Mir and/or an anti-sense oligonucleotide. As used herein an "RNAi molecule" is an RNA molecule that functions in RNA interference (e.g., siRNA, shRNA or DsiRNA). In certain embodiments, the present invention provides a method of treating a subject having an airway epithelial disease comprising administering to the subject an effective amount of a facilitating agent and an effective amount of a therapeutic agent to alleviate the symptoms of the airway epithelial disease by inducing a therapeutic effect. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effects can be measured quantitatively by a physician or qualitatively by a patient afflicted with the disease state targeted by the therapeutic agent.

In certain embodiments, the facilitating agent and/or therapeutic agent is administered orally, by inhalation, by aerosol, dry powder, bronchoscopic instillation, or intra-airway (tracheal or bronchial) aerosol. In certain embodiments, the therapeutic RNAi agent is present within a pharmaceutical composition. In certain embodiments, the airway epithelial disease is cystic fibrosis. In certain embodiments, the subject is a mammal, such as a human. In certain embodiments the symptoms are reduced by at least 1%, 5%, 10%, 20, 30%, 40%, 50%, 60%, 70%, 80%, 90% 95%, or 99%.

In certain embodiments, the cell is contacted on its mucosal surface.

In certain embodiments, the facilitating agent is present within a pharmaceutical composition.

In certain embodiments, the present invention provides a method of treating a subject having an airway epithelial disease comprising administering to the subject an effective amount of a facilitating agent and an effective amount of a therapeutic agent to alleviate the symptoms of the airway epithelial disease by inducing a therapeutic effect, wherein the facilitating agent comprises a Platelet-activating factor receptor (PAFR) ligand. In certain embodiments, the PAFR ligand is Platelet-activating factor receptor (PAF), lipooligosaccharide (LOS) and/or teichoic acid.

In certain embodiments, the subject is a mammal, such as a human.

In certain embodiments, the facilitating agent is administered orally or by inhalation.

In certain embodiments, the facilitating agent and/or therapeutic agent is administered by aerosol, dry powder, bronchoscopic instillation, or intra-airway (tracheal or bronchial) aerosol.

In certain embodiments, the therapeutic agent is present within a pharmaceutical composition.

In certain embodiments the symptoms are reduced by at least 1%, 5%, 10%, 20, 30%, 40%, 50%, 60%, 70%, 80%, 90% 95%, or 99%.

In certain embodiments, the airway epithelial disease is cystic fibrosis.

In certain embodiments, the facilitating agent and/or therapeutic agent is present within a pharmaceutical composition.

In certain embodiments, the therapeutic agent comprises an RNAi agent.

In certain embodiments, the therapeutic agent further comprises Aminoglutethimide, Biperiden, Diphenhydramine, Rottlerin, Midodrine, Thioridazine, Sulfadimethoxine, neostigmine bromide, Pyridostigmine, pizotifen, tyrophostin (AG-1478), valproic acid, Scriptaid or neomycin.

In certain embodiments, the present invention provides a therapeutic agent comprising RNAi molecules and a facilitating agent, wherein the agent comprises a Platelet-activating factor receptor (PAFR) ligand. In certain embodiments, the PAFR ligand is Platelet-activating factor receptor (PAF), lipooligosaccharide (LOS) and/or teichoic acid. In certain embodiments, the therapeutic agent further comprises Aminoglutethimide, Biperiden, Diphenhydramine, Rottlerin, Midodrine, Thioridazine, Sulfadimethoxine, neostigmine bromide, Pyridostigmine, pizotifen, tyrophostin (AG-1478), valproic acid, Scriptaid or neomycin.

In certain embodiments, the present invention provides a kit for reducing a level of a target mRNA in a well-differentiated airway epithelia cell comprising (a) a facilitating agent, (b) a therapeutic RNAi molecule, and (c) instructions for contacting the cell with the facilitating compound and the RNAi molecule to reduce the mRNA level of the target mRNA by at least 1% as compared to a control cell that has not been contacted with the facilitating compound.

Figure 1:
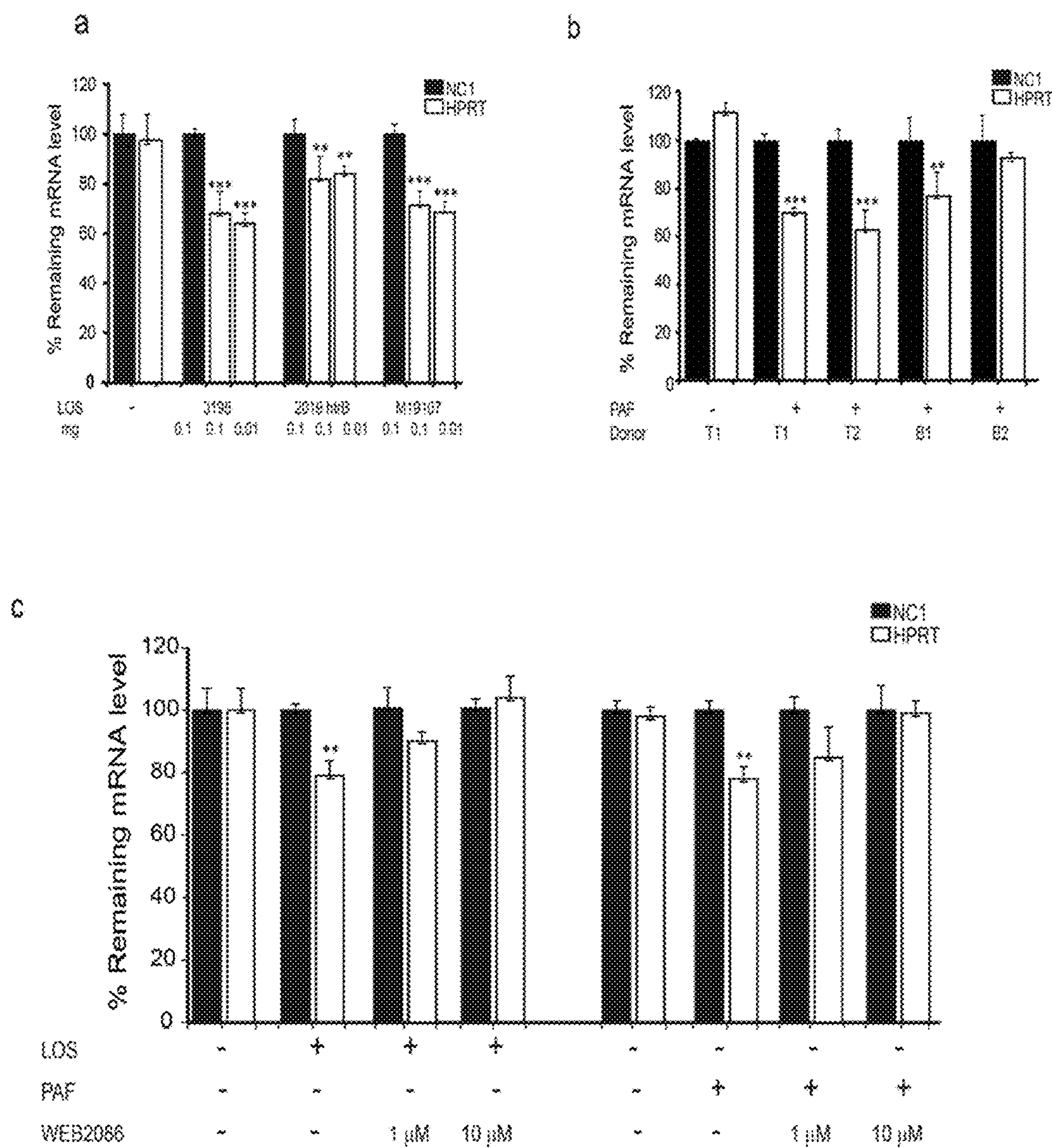
FIG. 1. LOS or PAF treatment with simultaneous HPRT DsiRNA-Transductin reduces mRNA levels in well-differentiated HAE. (a) Well-differentiated HAE cultures grown at the ALI were incubated in adding HPRT-targeting or control NC1 DsiRNA (250 nM) formulated with Transductin containing 0.1 or 0.01 mg LOS (HPRT-targeting DsiRNAs) or 0.1 mg LOS (NC1 DsiRNA). After 4 hours, the apical surface was rinsed and 24 hours later, target RNA levels quantified by RT-qPCR. All mRNA levels were normalized to NC1-treated samples. Mean levels were calculated from three biological replicates, each done in triplicate. *p<0.001, p<0.01 (Student's t-test). (b) Well-differentiated HAE from four different donors (T1, T1: tracheal epithelial culture; B1, B2: bronchial epithelial culture) were incubated with NC1 and HPRT DsiRNA and simultaneously treated with PAF at a concentration of 200 nM for 4 hours, after which the cells were rinsed and mRNA levels determined 24 hrs later. Samples were normalized to NC1-treated cells. *p<0.001, p<0.01 (Student's t-test). (c) Well-differentiated HAE were treated with PAFRa (WEB2086) at 1 or 10 μM for 2 hrs, followed by addition of DsiRNAs and Transductin (4 hours) with or without PAF (200 nM). PAFRa was present throughout transfection in cells pre-treated with the reagent. Cells were harvested and RNA quantified 24 hrs later. Samples were normalized to NC1-treated cells. **p<0.01 (Student's t-test).

Table 1 provides DsiRNA targets and sequences.

Table 2 provides qPCR primers and probes.

DETAILED DESCRIPTION OF THE INVENTION

Platelet Activating Factor Receptor (PAFR)

Platelet-activating factor receptor (PAF-R) is a Gq/G11-coupled-protein receptor that has a role in a wide range of biological processes such as vasodilation, superoxide formation, cell proliferation, angiogenesis and regulation of the inflammatory response. PAF-R is linked to multiple intracellular signaling pathways, including the p38 MAPK and PI 3-K pathways, through increasing intracellular calcium mobilization, increasing $IP_3$ synthesis and decreasing cAMP formation. Following PAFR activation, cells become rapidly desensitized and this refractory state is dependent on PAFR phosphorylation, internalization, and down-regulation. PAF-R has a wide biological distribution with high expression levels in the spleen and skeletal muscles and lower concentrations in the small intestine, lung, heart and liver.

PAFR Ligands

Lipooligosaccharides

Lipooligosaccharide (LOS) is the major component of the outer membrane of Gram-negative bacteria, contributing greatly to the structural integrity of the bacteria, and protecting the membrane from certain kinds of chemical attack. LPS also increases the negative charge of the cell membrane and helps stabilize the overall membrane structure. It is of crucial importance to gram-negative bacteria, whose death results if it is mutated or removed. LPS is an endotoxin, and induces a strong response from normal animal immune systems. It has also been implicated in non-pathogenic aspects of bacterial ecology, including surface adhesion, bacteriophage sensitivity, and interactions with predators such as amoebae. Finally, LOS molecules are responsible for the ability of some bacterial strains to display molecular mimicry and antigenic diversity, aiding in the evasion of host immune defenses and thus contributing to the virulence of these bacterial strains.

Teichoic Acid

Teichoic acids are found within the cell wall of Gram-positive bacteria such as species in the genera *Staphylococcus, Streptococcus, Bacillus, Clostridium, Corynebacterium*, and *Listeria*, and appear to extend to the surface of the peptidoglycan layer. Teichoic acids are not found in Gram-negative bacteria. They can be covalently linked to N-acetylmuramic acid of the peptidoglycan layer, to the lipids of the cytoplasmic membrane, or to a terminal D-alanine in the tetrapeptide crosslinkage between N-acetylmuramic acid units. Lipoteichoic acids also act as receptor molecules for some Gram-positive bacteriophage.

LOS and Teichoic Acid, along with PAF, are known ligands for PAFR and are used by *Haemophilus influenzae* and *S. pneumoniae*, respectively to gain entry into airway epithelial cells to initiate bacterial infection.

RNA Interference (RNAi) Molecules

RNA interference (RNAi) is a powerful method to affect the abundance of a cellular protein. The delivery of RNAi oligonucleotides to airway epithelia has the potential to manipulate gene expression for therapeutic ends, and may be useful for diseases such as asthma, chronic obstructive pulmonary disease (COPD), and cystic fibrosis. However, inefficient delivery of reagents to target cells has hampered this line of therapeutic investigation.

It has been found that once airway epithelial cells become well differentiated, their barrier properties remarkably inhibit the uptake of RNAi oligonucleotides delivered to the mucosal surface of the cells in a variety of different formulations. The treatment of well differentiated airway epithelia by applying with certain facilitating agents increased the uptake of RNAi oligonucleotides, and effected genes silencing. This approach is used to enhance the delivery of therapeutic oligonucleotides to the airways.

In certain embodiments, the present invention provides methods of reducing a level of a target mRNA in a well-differentiated airway epithelia cell comprising contacting the cell with a facilitating agent (i.e., a PAFR ligand) followed by contacting the cell with a therapeutic RNAi agent, wherein the mRNA level of the target mRNA is reduced by at least 1% as compared to a control cell that has not been contacted with the facilitating compound.

RNAi consists of the use of exogenous sources of RNA to down-regulate the expression of specific proteins in a targeted manner. This is accomplished by creating an RNA sequence of about 20 bp in length that will specifically bind to nascent RNA being produced by the cell type of interest. The RNA dimer activates endogenous nucleases that destroy the RNA. The goal of this technique is to prevent translation of the message into protein that performs a function that is unwanted to therapeutic or research reasons.

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest. As used herein, the term "siRNA" is a generic term that encompasses the subset of shRNAs and miRNAs. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

As used herein, Dicer-substrate RNAs (DsiRNAs) are chemically synthesized asymmetric 25-mer/27-mer duplex RNAs that have increased potency in RNA interference compared to traditional siRNAs. Traditional 21-mer siRNAs are designed to mimic Dicer products and therefore bypass interaction with the enzyme Dicer. Dicer has been recently shown to be a component of RISC and involved with entry of the siRNA duplex into RISC. Dicer-substrate siRNAs are designed to be optimally processed by Dicer and show increased potency by engaging this natural processing pathway. Using this approach, sustained knockdown has been regularly achieved using sub-nanomolar concentrations. (U.S. Pat. No. 8,084,599; Kim et al., Nature Biotechnology 23:222 2005; Rose et al., Nucleic Acids Res., 33:4140 2005).

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional siRNAs. "Artificial miRNA" or an "artificial miRNA shuttle vector", as used herein interchangably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (~35 nucleotides upstream and ~40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

"Off-target toxicity" refers to deleterious, undesirable, or unintended phenotypic changes of a host cell that expresses or contains an siRNA. Off-target toxicity may result in loss of desirable function, gain of non-desirable function, or even death at the cellular or organismal level. Off-target toxicity may occur immediately upon expression of the siRNA or may occur gradually over time. Off-target toxicity may occur as a direct result of the expression siRNA or may occur as a result of induction of host immune response to the cell expressing the siRNA. Without wishing to be bound by theory, off-target toxicity is postulated to arise from high levels or overabundance of RNAi substrates within the cell. These overabundant or overexpressed RNAi substrates, including without limitation pre- or pri RNAi substrates as well as overabundant mature antisense-RNAs, may compete for endogenous RNAi machinery, thus disrupting natural miRNA biogenesis and function. Off-target toxicity may also arise from an increased likelihood of silencing of unintended mRNAs (i.e., off-target) due to partial complementarity of the sequence. Off target toxicity may also occur from improper strand biasing of a non-guide region such that there is preferential loading of the non-guide region over the targeted or guide region of the RNAi. Off-target toxicity may also arise from stimulation of cellular responses to dsRNAs which include dsRNA (IFN-b, PKR, OAS 1). "Decreased off target toxicity" refers to a decrease, reduction, abrogation or attenuation in off target toxicity such that the therapeutic effect is more beneficial to the host than the toxicity is limiting or detrimental as measured by an improved duration or quality of life or an improved sign or symptom of a disease or condition being targeted by the siRNA. "Limited off target toxicity" or "low off target toxicity" is used to refer to an unintended undesirable phenotypic changes to a cell or organism, whether detectable or not, that does not preclude or outweigh or limit the therapeutic benefit to the host treated with the siRNA and may be considered a "side effect" of the therapy. Decreased or limited off target toxicity may be determined or inferred by comparing the in vitro analysis such as Northern blot or QPCR for the levels of siRNA substrates or the in vivo effects comparing an equivalent shRNA vector to the miRNA shuttle vector of the present invention.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where siRNA molecules have not been administered). Knock-down of gene expression can be directed by the use of dsRNAs or siRNAs.

"RNA interference (RNAi)" is the process of sequence-specific, post-transcriptional gene silencing initiated by siRNA. During RNAi, siRNA induces degradation of target mRNA with consequent sequence-specific inhibition of gene expression.

According to a method of the present invention, the expression of a target gene product can be modified via RNAi. For example, the accumulation of the gene product can be suppressed in a cell. The term "suppressing" refers to the diminution, reduction or elimination in the number or amount of transcripts present in a particular cell. For example, the accumulation of mRNA encoding a gene product can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single-stranded or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid nucleic acid molecules and compositions containing those molecules. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The term "chimeric" refers to a gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfectly complimentary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell.

"cDNA" refers to a single- or a double-stranded DNA that is complementary to and derived from mRNA.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Antisense inhibition" refers to the production of antisense RNA transcripts capable of suppressing the expression of protein from an endogenous gene or a transgene.

As used herein, "sequence identity" or "identity" in the context of two nucleic acid sequences makes reference to a specified percentage of nucleotides in the two sequences that are the same when aligned for maximum correspondence over a specified region.

The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using standard parameters.

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

Administration of Facilitating and Therapeutic Agents

Utilizing Platelet Activating Factor Receptor as an Entry Point for siRNA into Airway Epithelial Cells Certain embodiments of the present technology use the co-treatment of PAF, LOS and/or teichoic acid to facilitate entry of RNAi molecules into target airway epithelial cells. Once inside the cell, the siRNA molecules specifically bind target mRNA molecules resulting in their destruction. This is used clinically to decrease the expression levels of genes in the airway epithelial cells that are associated with disease, thus limiting or preventing the effects of that disease. Experimental data demonstrates ~35-40% reduction in target mRNA in the airway epithelial model with use of these agents compared to negligible affects in their absence.

In certain embodiments, the present invention provides methods of using therapeutic agents to treat cystic fibrosis.

The facilitating agent and therapeutic agent are administered to the patient so that the facilitating and therapeutic agents contact cells of the patient's respiratory or digestive system. For example, the facilitating and/or therapeutic agent may be administered directly via an airway to cells of the patient's respiratory system. The facilitating and therapeutic agents can be administered intranasally (e.g., nose drops) or by inhalation via the respiratory system, such as by propellant based metered dose inhalers or dry powders inhalation devices.

Formulations suitable for administration include liquid solutions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. The therapeutic agent can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

The facilitating and therapeutic agents, alone or in combination with other suitable components, can be made into aerosol formulations to be administered via inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer. In certain embodiments, administration may be, e.g., aerosol, instillation, intratracheal, intrabronchial or bronchoscopic deposition.

In certain embodiments, the facilitating and/or therapeutic agent may be administered in a pharmaceutical composition. Such pharmaceutical compositions may also comprise a pharmaceutically acceptable carrier and other ingredients known in the art. The pharmaceutically acceptable carriers described herein, including, but not limited to, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices. Viscoelastic gel formulations with, e.g., methylcellulose and/or carboxymethylcellulose may be beneficial (see Sinn et al., *Am J Respir Cell Mol Biol,* 32(5), 404-410 (2005)).

The facilitating and therapeutic agents can be administered by any conventional method available for use in conjunction with pharmaceuticals, either as individual therapeutic agents or in combination with at least one additional therapeutic agent.

In certain embodiments, the facilitating and therapeutic agents are administered with an agent that disrupts, e.g., transiently disrupts, tight junctions, such as EGTA (see U.S. Pat. No. 6,855,549).

The total amount of the facilitating and therapeutic agents administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

The facilitating and therapeutic agents can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The facilitating and therapeutic agents may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the therapeutic agent can be determined by comparing their in vitro activity, and in vivo activity in animal models. Methods for the extrapolation of effective dosages in mice, and other animals, to humans are known to the art; for example, see U.S. Pat. No. 4,938,949.

The amount of the facilitating and therapeutic agents, or an active salt or derivative thereof, required for use in treatment will vary not only with the particular salt selected but also with the route of administration, the nature of the condition being treated and the age and condition of the patient and will be ultimately at the discretion of the attendant physician or clinician.

Pharmaceutical compositions are administered in an amount, and with a frequency, that is effective to inhibit or alleviate the symptoms of airway epithelial disease (e.g., cystic fibrosis) and/or to delay the progression of the disease. The effect of a treatment may be clinically determined by nasal potential difference measurements as described herein. The precise dosage and duration of treatment may be determined empirically using known testing protocols or by testing the compositions in model systems known in the art and extrapolating therefrom. Dosages may also vary with the severity of the disease. A pharmaceutical composition is generally formulated and administered to exert a therapeutically useful effect while minimizing undesirable side effects. In general, an oral dose ranges from about 200 mg to about 1000 mg, which may be administered 1 to 3 times per day. Compositions administered as an aerosol are generally designed to provide a final concentration of about 10 to 50 μM at the airway surface, and may be administered 1 to 3 times per day. It will be apparent that, for any particular subject, specific dosage regimens may be adjusted over time according to the individual need. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful to treat cystic fibrosis. Examples of such agents include antibiotics. Accordingly, in one embodiment the invention also provides a composition comprising a therapeutic agent, or a pharmaceutically acceptable salt thereof, at least one other therapeutic agent, and a pharmaceutically acceptable diluent or carrier. The invention also provides a kit comprising a therapeutic agent, or a pharmaceutically acceptable salt thereof, at least one other therapeutic agent, packaging material, and instructions for administering the therapeutic agent or the pharmaceutically acceptable salt thereof and the other therapeutic agent or agents to an animal to treat cystic fibrosis.

A pharmaceutical composition may be prepared with carriers that protect active ingredients against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

In certain embodiments, the facilitating and therapeutic agents are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and to improve solubility.

As noted above, facilitating and therapeutic agents may be administered to a mammal to stimulate chloride transport, and to treat cystic fibrosis. Patients that may benefit from administration of a therapeutic compound as described herein are those afflicted with cystic fibrosis. Such patients may be identified based on standard criteria that are well known in the art, including the presence of abnormally high salt concentrations in the sweat test, the presence of high nasal potentials, or the presence of a cystic fibrosis-associated mutation. Activation of chloride transport may also be beneficial in other diseases that show abnormally high mucus accumulation in the airways, such as asthma and chronic bronchitis. Similarly, intestinal constipation may benefit from activation of chloride transport by the therapeutic agents provided herein.

The term "therapeutically effective amount," in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat," "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

Example 1

Well-differentiated human airway epithelia (HAE) present formidable barriers to efficient siRNA delivery. We previously reported that treatment of airway epithelia with specific small molecules improves oligonucleotide uptake and facilitates RNAi responses. Here, we exploited the platelet activating factor receptor (PAFR) pathway, utilized by specific bacteria to transcytose into epithelia, as a trigger for internalization of Dicer-substrate siRNAs (DsiRNA). PAFR is a G-protein coupled receptor which can be engaged and activated by phosphorylcholine residues on the lipooligosaccharide of non-typeable *Haemophilus influenzae* (NTHi) and the teichoic acid of *Streptococcus pneumoniae* as well as by its natural ligand, platelet activating factor (PAF). When well-differentiated airway epithelia were simultaneously treated with either NTHi lipooligosaccharide or PAF and transduced with DsiRNA formulated with the peptide Transductin, we observed silencing of both endogenous and exogenous targets. PAF receptor antagonists prevented LOS or PAF-assisted DsiRNA silencing, demonstrating that ligand engagement of PAFR is essential for this process. Additionally, PAF-assisted DsiRNA transfection decreased CFTR protein expression and function and reduced exogenous viral protein levels and titer in HAE. Treatment with spiperone, a small molecule identified using the connectivity map database to correlate gene expression changes in response to drug treatment with those associated with PAFR stimulation, also induced silencing. These results suggest that the signaling pathway activated by PAFR binding can be manipulated to facilitate siRNA entry and function in difficult to transfect well-differentiated airway epithelial cells.

Introduction

Small interfering RNA (siRNA) oligonucleotides cannot easily cross cellular membranes because of their size and negative charge. The efficient delivery of siRNA oligonucleotides remains a major challenge for advancing RNA interference (RNAi) technology, particularly to the airway. Although the airways can support direct topical delivery, both extra- and intracellular barriers present obstacles for successful RNAi therapy [1, 2]. While several studies reported therapeutic effects following naked siRNA delivery to the lungs [3-12] others have suggested alternative off target explanations for the results [7, 9, 13, 14]. Additional data support these findings; siRNA oligonucleotides enter cell poorly, and as a result are not well retained in the respiratory epithelium [15, 16].

We also reported earlier that Dicer-substrate siRNA (DsiRNA) formulations failed to silence genes in well-differentiated airway epithelia, irrespective of the dose or time of transfection, and that this lack of efficiency correlated strongly with limited oligonucleotide entry [17]. However, we discovered that pretreatment with certain small molecules, as well as enhancers of macropinocytosis such as epidermal growth factor, improved synthetic oligonucleotide uptake and RNAi responses. This result suggested that mechanisms promoting siRNA oligo internalization into differentiated airway epithelia might facilitate RNAi responses.

In this work, we considered mechanisms that microorganisms exploit to enter cells. Following receptor binding, many viruses and bacteria cross cell membranes by one or more endocytic pathway including phagocytosis, clathrin- or caveolae-mediated endocytosis, or macropinocytosis [18, 19]. An elegant study by Ketterer et. al [18] showed that the opportunistic pathogen of the airway, nontypeable *Haemophilus Influenzae* (NTHi), entered human bronchial epithelia by macropinocytosis after initiating cytoskeletal rearrangement. Further study by the same group demonstrated that NTHi invaded host cells by first binding to the host receptor platelet activating factor receptor (PAFR) via its lipooligosaccharide [20] glycoforms containing phosphorylcholine [21] [22]. The adherence and invasion of another bacterium, *Streptococcus pneumoniae* (pneumococcus) was also linked to PAFR binding [23], possibly through the ChoP moiety present in the bacterial cell wall. Thus, the bacteria's interaction with PAFR provides for cell entry.

PAFR is a G-protein coupled receptor whose natural ligand is platelet activating factor (PAF), a potent phospholipid which also consists of the ChoP moiety in NTHi and the pneumococcal cell wall. Since PAFR stimulation is involved in bacterial entry [24], we hypothesized that PAFR activation might also facilitate macromolecules entry such as siRNA.

We tested this hypothesis on well-differentiated human airway epithelia (HAE) grown at the air-liquid interface (ALI) and assessed the ability of DsiRNAs to silence endogenous or exogenous targets with or without PAFR stimulation. We show that DsriRNA transfection in combination with PAFR engagement by any of its cognate binding partners or by small molecule treatment improves DsiRNA uptake with concomitant reductions in target RNA and protein levels.

Results

Transfection of DsiRNA into HAE Along with LOS or PAF Treatment Results in Silencing of mRNA Levels of Target Gene.

Well-differentiated primary cultures of human airway epithelia maintained at the ALI model many aspects of the in vivo morphology of the surface epithelium and are a useful system in which to test the efficacy of inhibitory RNAs in the form of DsiRNAs [25]. We previously reported that DsiRNA transfection in formulation with various transfection agents failed to achieve RNAi in HAE [17]. To test if DsiRNA entry and RNAi responses in HAE can be improved, we activated PAFR in airway cells using some of its cognate binding partners.

One PAFR ligand is the LOS structure of NTHi. The NTHi LOS contains a highly variable assortment of short polyhexose or lactosamine chains emanating from a triheptose-ketodeoxyoctanoate-phosphate-lipid A core region [26]. In a form of molecular mimicry, NTHi expresses host carbohydrate structures within the oligosaccharide portion of the LOS, including ChoP. NTHi can adhere to and invade human bronchial epithelial cells via interactions between the ChoP$^+$ LOS glycoforms and PAFR [22]. We isolated LOS from the native NTHi strains and the three LOS isoforms tested differed in the number of phosphocholine residues and LOS stability. When HAE were transduced with a HPRT DsiRNA-Transductin formulation and simultaneously treated with each LOS, HPRT mRNA levels were reduced by up to 35% when analyzed 24 hours after transfection (FIG. 1*a*) compared to negligible transduction in the absence of the LOS.

Figure 7:
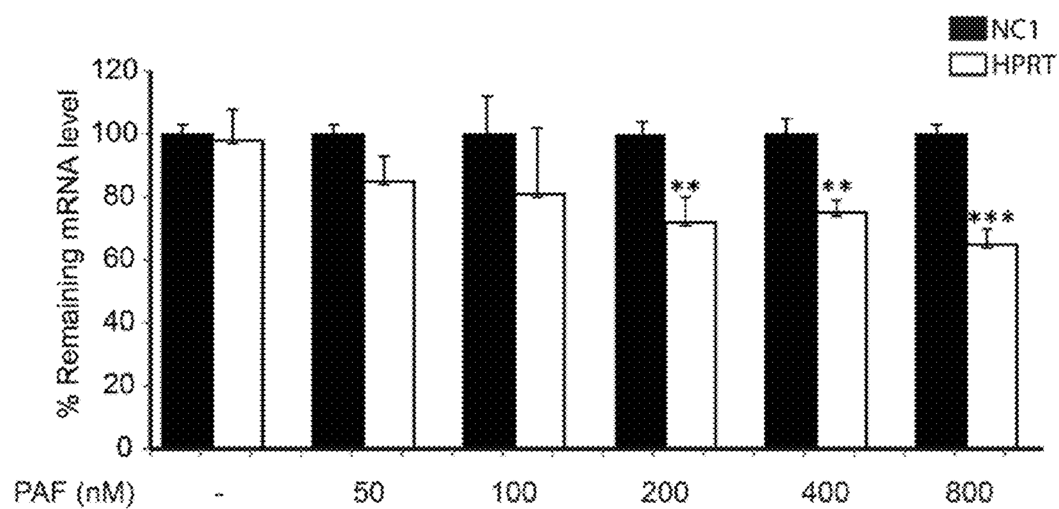
FIG. 7: Effect of different doses of PAF on Transductin-DsiRNA delivery in HAE. The cells were transduced with Transductin complexed with HPRT DsiRNA and simultaneously treated with PAF at the indicated concentration for a period of 4 hours. The cells were harvested 24 hours later for RT-qPCR. The data show HPRT mRNA levels normalized to NC1-treated samples (three biological replicates—in triplicate). *p<0.001, p<0.03 (Student's t-test).

The natural ligand for PAFR is the potent phospholipid activator, PAF. We hypothesized that PAF activation of PAFR during DsiRNA transduction would improve RNAi responses in HAE as seen with LOS. PAF binding to PAFR activates several signaling mechanisms including GTPase activation causing phospholipid turnover (via phospholipases C, D, and A2 pathways) and protein kinase C and tyrosine kinase activation[27]. Epithelia were PAF treated for 4 hours in the presence of the DsiRNA mixture, rinsed, and then incubated for a further 24 hours before gene expression was measured by RT-qPCR. Treatment of HAE with DsiRNA-Transductin and PAF reduced HPRT mRNA levels between 10% and 40% depending on the donor cell culture (FIG. 16). A dose-response relationship for PAF on DsiRNA silencing was observed (FIG. 7). We also investigated the duration of knock down after PAF-assisted transfection. Following delivery, epithelia were studied on days 1, 3, 6, and 10. HPRT mRNA levels were significantly reduced 1 and 3 days post transfection. By 6 and 10 days the transcript levels were returning to basal levels. Since each mRNA target is likely to have a different rate of turnover, repeated transfection may be necessary to maintain knock-down.

Figure 8:
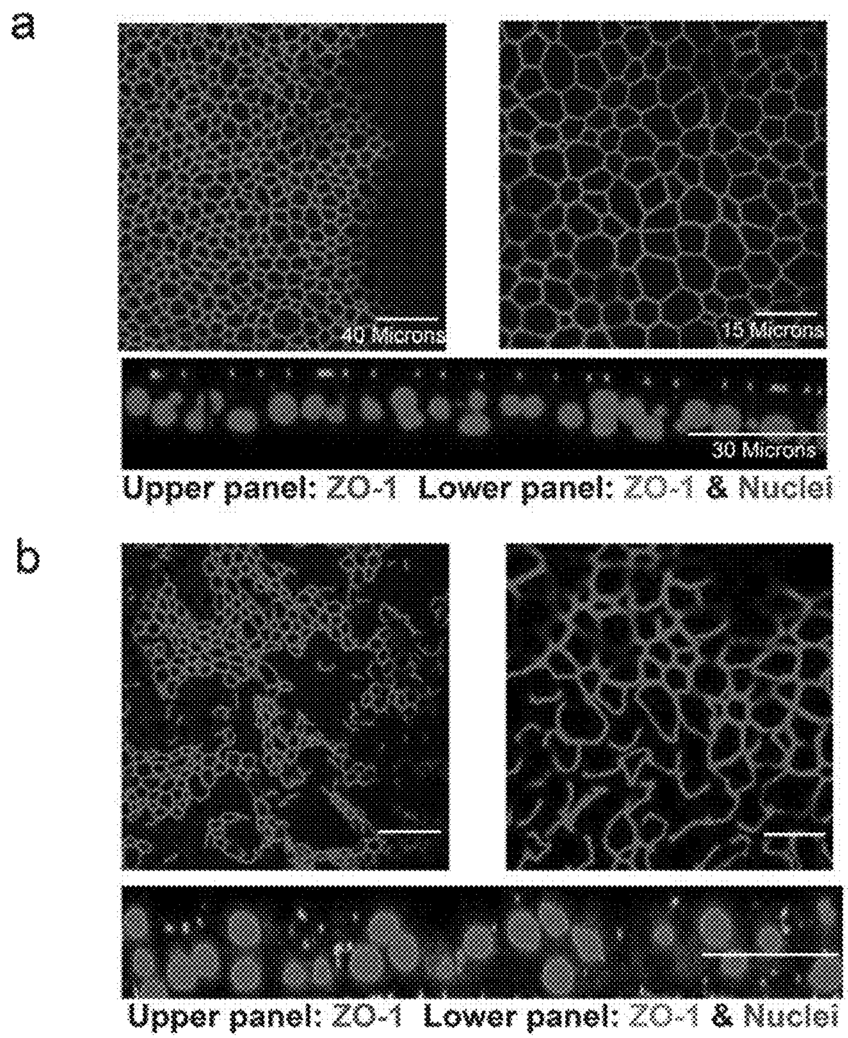
FIG. 8. The effect of PAF on tight junction integrity in HAE. PAF was added to the apical surface at a concentration of 200 nM. The cells were fixed at the end of either 8 hours (a) or 24 hours (b) and then stained for nuclei and tight junctional protein ZO-1. The cells were then visualized by confocal microscopy. In each, top panel: x-y and bottom panel: x-z.

A well-studied effect of PAFR stimulation is the activation of mediators that can generate inflammatory responses (38-41). As a mediator of inflammation, PAFR activation can alter tight junction integrity in endothelial and intestinal epithelial cells [28, 29]. We examined the effects of PAF on tight junction integrity in airway epithelia. PAF application to the apical and basolateral surfaces of HAE for 8 hours caused no alteration of tight junction morphology as assessed by ZO-1 immunostaining. In contrast, 24 hour of PAF treatment caused significant alterations in tight junction morphology (FIG. 8*a*). Our experimental protocol involved PAF treatment of epithelia during DsiRNA transduction for 4 hours; hence its effects on tight junction should be minimized. We also examined epithelial cell morphology after PAF-assisted transfection. Epithelial sheets were fixed, sectioned, and stained with hematoxylin-eosin (H&E) 1 and 10 days after transfection showed no changes in cell morphology when compared to control treated epithelium (FIG. 8*b*). Cytotoxicity was also assessed by lactate dehydrogenase release. Both PAF and control treated cells showed minimal evidence of cytotoxicity.

The PAFR-dependence of the LOS- and PAF-mediated enhancement of DsiRNA silencing was evaluated using the PAF receptor antagonist (PAFRa) WEB2086. Pre- or post-treatment of epithelia with 100 μM PAFRa completely inhibited HPRT silencing of either LOS- or PAF-assisted transduction samples (FIG. 1*c*). Lower concentrations of PAFRa (1 μM) partially inhibited silencing in cells transduced with LOS or PAF (FIG. 1*c*). These results suggest that the effects of LOS and PAF on siRNA-mediated silencing are a consequence of their interactions with PAFR.

PAF Treatment Enhances DsiRNA Entry and Uptake into Cells.

Figure 2:
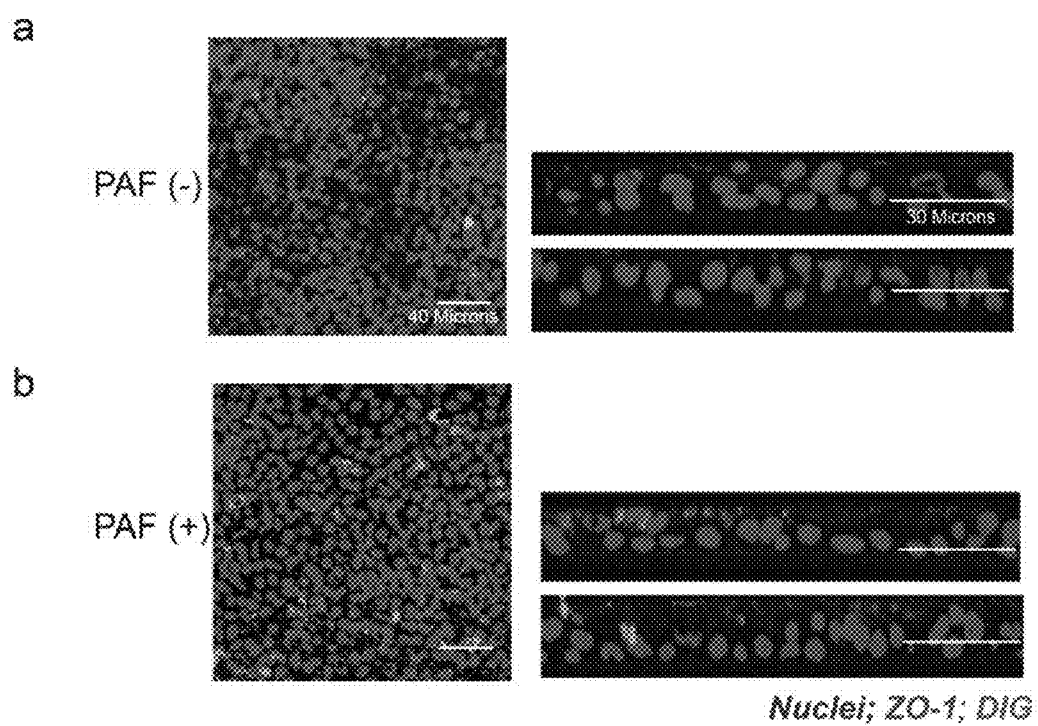
FIG. 2. PAF treatment enhances DsiRNA entry and uptake into cells. Confocal images (x-y, left panels; x-z stacks, right panels) of epithelia 1 hour after transduction with DIG-labeled DsiRNA complexed with Transductin, without (a) or with (b) PAF treatment (200 nM). Blue, nuclei; green, DIG-labeled oligo. The images on the right and the left are from different fields.

We next asked whether the improved RNAi responses following PAFR stimulation were due to an increase in uptake and internalization of DsiRNA. When digoxigenin (DIG)-labeled DsiRNA was transduced in formulation with Transductin in PAF-treated HAE, we observed a substantial increase in the amount of internalized label 1 hour later (FIG. 2*b*) compared with control HAE (FIG. 2*a*). These data suggests that improved RNAi upon PAFR stimulation is a result of improved DsiRNA internalization.

Spiperone Treatment Induces RNAi Responses in HAE.

Figure 3:
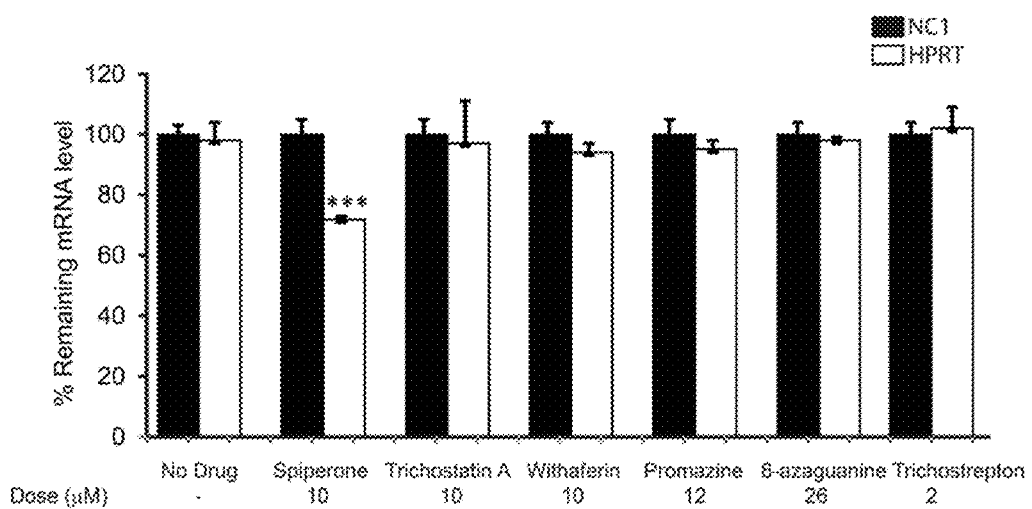
FIG. 3. Spiperone improves RNAi responses in DsiRNA transduced cells. HAE were pre-treated with various small molecules at the concentration indicated. The drugs were added to the apical surface and the basolateral media for 6 hours. Both surfaces were then washed and HPRT or NC1 DsiRNA formulated with Transductin added to the apical surface. The cells were washed after 4 hours, and RT-qPCR done on cell lysates harvested 24 hours later. Data show HPRT mRNA levels normalized to NC1-treated samples (three biological replicates—in triplicate). ***p<0.001 (Student's t-test).
Figure 9:
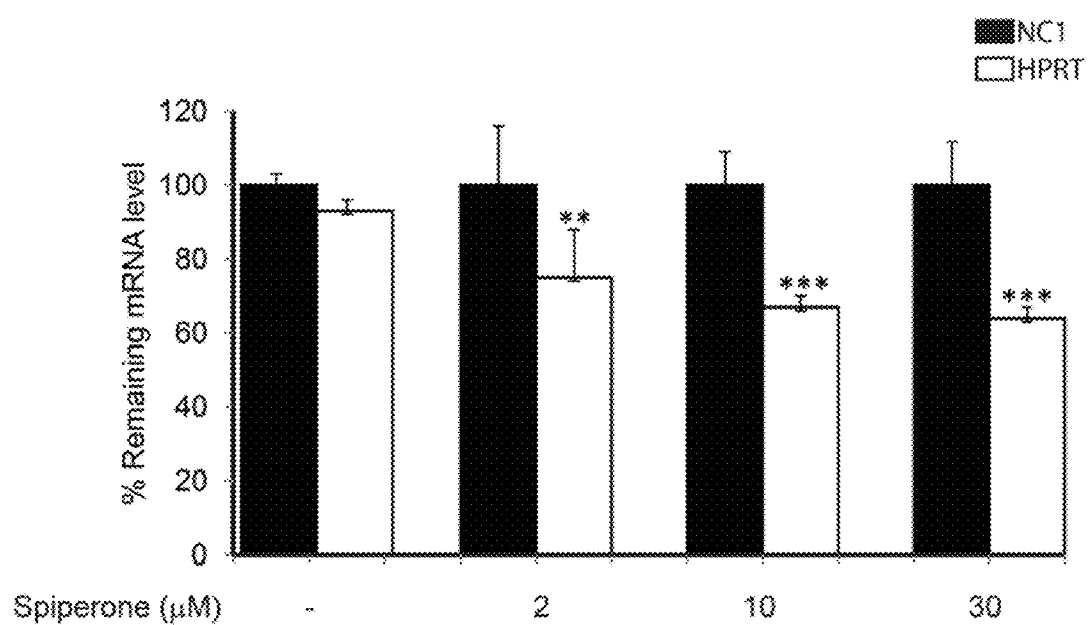
FIG. 9: Dose response effect of spiperone on Transductin-DsiRNA delivery in HAE. The cells were treated with spiperone at the indicated concentration for a period of 6 hours. Transduction with DsiRNATransductin complex was performed and the cells were harvested 24 hours later. After RT-qPCR, the data was analyzed by normalizing HPRT mRNA levels to NC1-treated samples (three biological replicates—in triplicate). ***p<0.001, p<0.03 (Student's t-test).

The Connectivity map (CMAP) database is a repository of transcriptional profiles from a number of human cell lines in response to drug treatments [30]. We correlated the input signatures of gene expression changes during PAFR activation from a previously published microarray study [31] with those from the CMAP database. The method of analysis is described in more detail in the Materials and Methods. The analysis yielded several drugs that correlated positively with PAF-induced changes in gene expression. We reasoned that treatment of HAE with these candidates might induce gene expression changes similar to those associated with PAFR activation. From these data, 6 candidates were selected and tested. HAE were pretreated with drugs and then subsequently incubated with HPRT targeting DsiRNA-Transductin formulations as before. Of these interventions, only spiperone pretreatment was effective. Spiperone, an antipsychotic drug, increases intracellular $Ca^{2+}$ levels through a protein kinase-coupled phospholipase C-dependent pathway and also stimulates calcium-activated chloride channels in polarized human airway epithelial cells [32]. Of note, PAF also activates the phospholipase C pathway [27]. Spiperone treatment of epithelia (10 μM) before DsiRNA transduction resulted in 25% silencing of HPRT mRNA levels (FIG. 3). A spiperone dose-response showed marginal increases in silencing with increasing doses (FIG. 9).

PAF or Spiperone Treatment Decreases CFTR Protein Levels and Function in HAE Transduced with CFTR DsiRNA.

Figure 4:
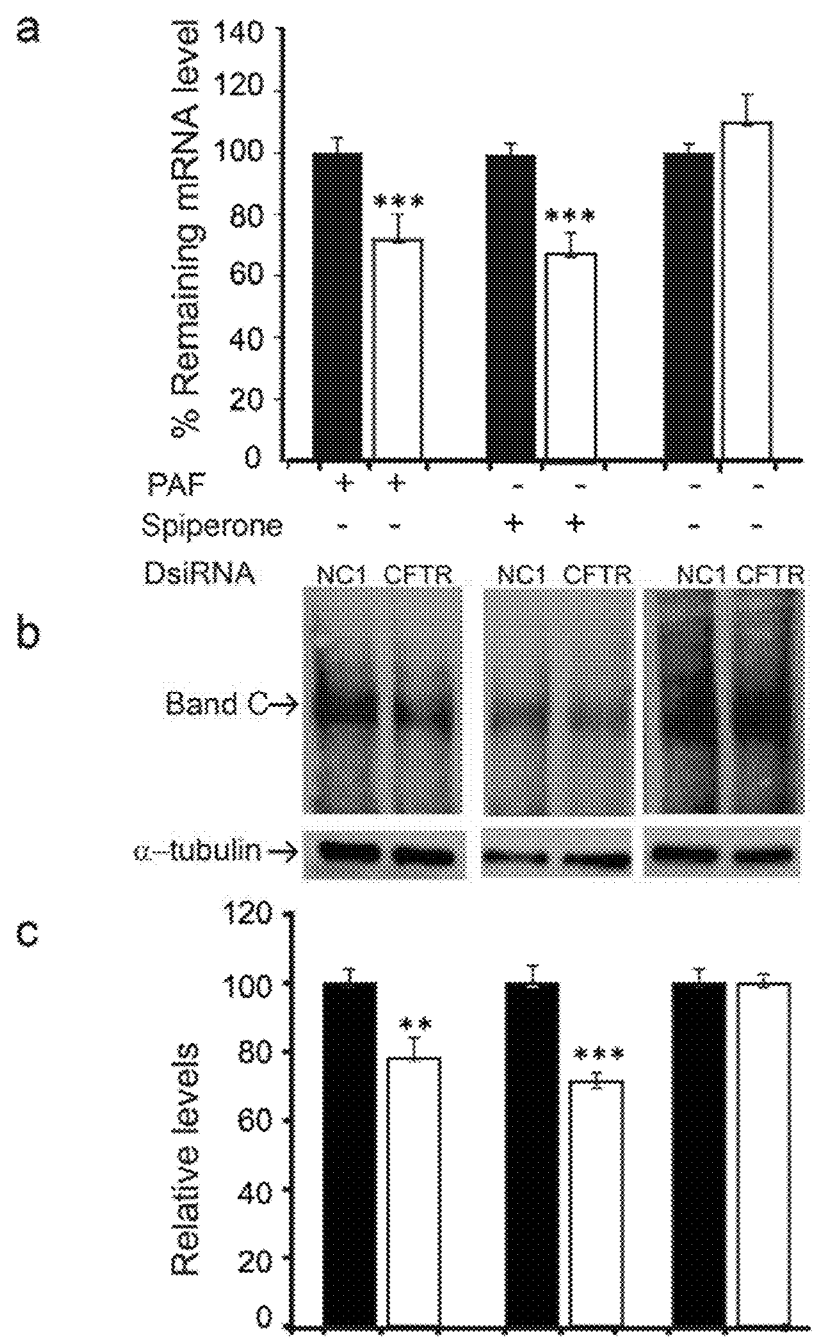
FIG. 4. PAF or spiperone treatment decreases CFTR protein levels in HAE treated with CFTR DsiRNA. (a) PAF and DsiRNA (CFTR-targeting or control NC1 in Transductin), were applied to well-differentiated HAE for 4 hours. Alternatively, spiperone was applied apically and basolaterally to well-differentiated HAE for 6 hours, and then removed by rinsing before incubation for 4 hours with CFTR-targeting or NC1 DsiRNAs complexed with Transductin. In both cases, 24 hours after transfection, and RNA levels quantified by RT-qPCR. (b) A representative immunoblot from similarly treated wells, but cells were lysed and proteins visualized after immunoprecipitation with anti-CFTR antibody. Alpha-tubulin was used as a loading control. (c) Densitometry readings of immunoblots with results normalized to NC1 treated samples. In all cases, data are from 3 biological replicates and are mean±SD. *p<0.001, p<0.01 (Student's t-test).

We next asked whether endogenous gene silencing by DsiRNA, facilitated by PAFR activation, reduces target mRNA and protein levels. CFTR encodes an anion channel in airway epithelia. Loss of CFTR function, caused by mutations in the CFTR gene causes cystic fibrosis, an important chronic disease characterized by progressive pulmonary infection and inflammation. DsiRNA incubation with simultaneous PAF treatment or with spiperone pretreatment caused approximately 30% silencing of CFTR mRNA levels (FIG. 4*a*). Immunoprecipitation and then western blot analysis in cells treated with PAF or spiperone and CFTR DsiRNA-Transductin showed reduced CFTR protein levels compared to controls (FIG. 4*b*). Fully glycosylated CFTR band C was significantly decreased in PAF and spiperone treated cells (FIG. 4*c*). Consequently, well-differentiated airway epithelia allows for silencing of target mRNA and protein when PAFR signaling or PAFR related gene expression changes are activated.

Figure 5:
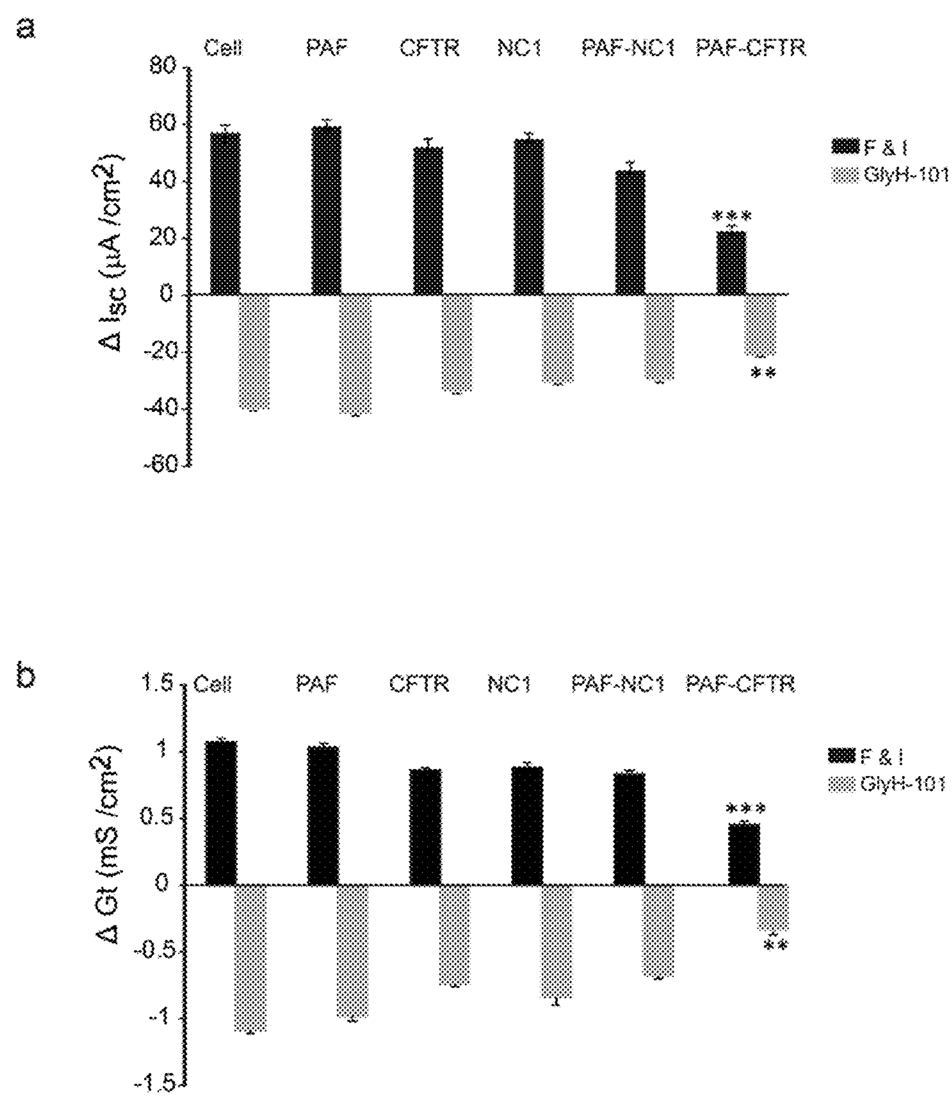
FIG. 5. PAF treatment with CFTR DsiRNA reduces CFTR function in HAE. Changes in transepithelial resistance (AIsc) (a) and conductance (AGt)(b) induced by sequential addition of amiloride, Forskolin & IBMX (F&I) and GlyH-101 in HAE cultures treated with indicated agents. Each bar represents nine replicates from three different donors (3 replicates from each). Mean±SD. Statistically significant difference *p<0.001, p<0.01 (Student's t-test).

We next assessed epithelial cell bioelectric properties following PAF-mediated delivery of DsiRNA-Transductin targeting CFTR; CFTR is a phosphorylation and nucleotide activated anion channel that helps regulate the volume and composition of airway surface liquid, and loss of function impairs transepithelial anion transport. In control epithelia with or without PAF treatment (without HPRT DsiRNA transfection) or PAF and scrambled control DsiRNA (NC1) treated cells, the addition forskolin and isobutylmethylxantine (IBMX) increased the cAMP-activated transepithelial short-circuit current (Isc and ΔIsc) and conductance (Gt and AGt) as expected (FIGS. 5*a,b*). Subsequent addition of GlyH-101, a CFTR channel inhibitor, decreased both values. In contrast, PAF treated and CFTR DsiRNA transduced cells showed significantly reduced cAMP-activated changes in transepithelial current and conductance (FIGS. 5*a,b*). We note that CFTR activity is typically not rate-limiting at normal levels of CFTR expression. Rather, the activity of transporters/channels at the basolateral membrane limits the magnitude of agonist activated current. Therefore, the magnitude of current reduction observed here may reflect a reduction in CFTR protein expression greater than that suggested by current measurements. These results show that PAFR-mediated oligo delivery and CFTR knockdown significantly reduced CFTR channel activity.

PAF Treatment Reduces Exogenous Viral Protein with Concomitant Decrease in Titer in DsiRNA Transduced HAE.

Figure 6:
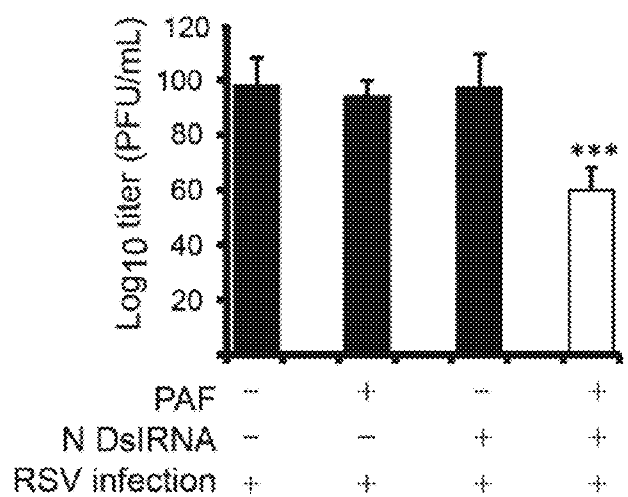
FIG. 6. PAF induced DsiRNA uptake reduces RSV protein levels and titer in HAE. HAE was either treated or untreated with PAF in concurrence with RSV N DsiRNA. Six hours later the cells were infected with RSV at an MOI of 1. Forty eight hours later, the cell washings from the apical surface was collected and assayed for viral titer (a). The cells were lysed and the proteins visualized after immunoprecipitation with anti-RSV antibodies (b) and the bands quantified by densitometry (c). Data are mean±SD from the results three different experiments, each using a different donor. ***p<0.001 (Student's t-test).
Figure 6:
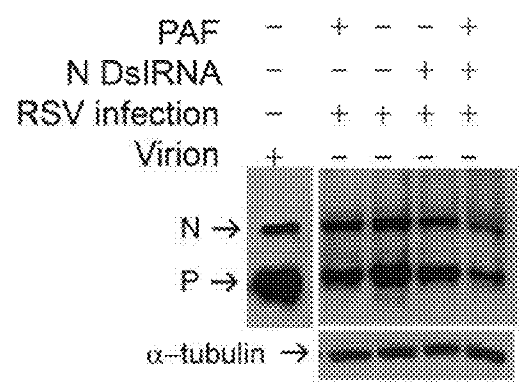
Figure 6:
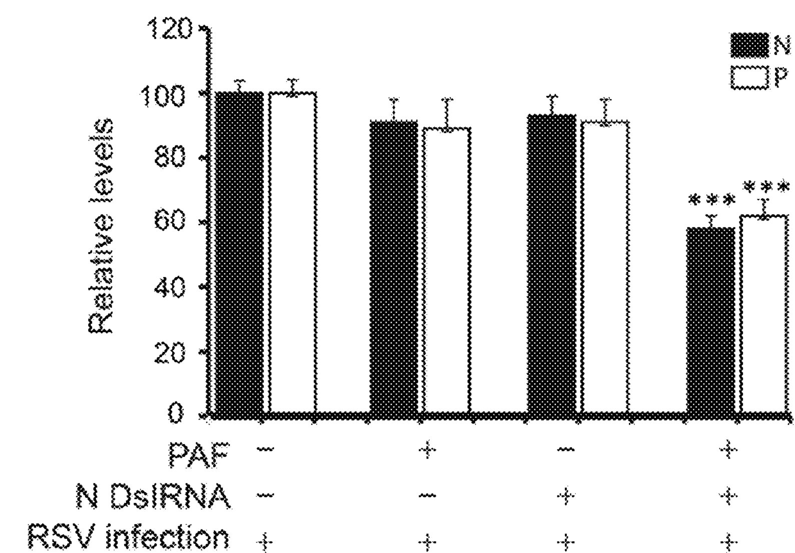

Respiratory Syncytial Virus (RSV) is an important pathogen in children and elderly and immunocompromised individuals. There is neither a preventive vaccine nor an effective treatment for the disease. Potent RNAi against RSV in airway epithelia has not been rigorously demonstrated. Here, we tested the effect of DsiRNA against the RSV N gene in infected HAE with or without PAF treatment at the time of oligonucleotide application. Epithelia were PAF treated and incubated with DsiRNA-Transductin targeting the N gene. Six hours later the cells were infected with RSV at an MOI of 1. Viral titers calculated from the apical rinses were reduced more than 100-fold in samples treated with PAF (FIG. 6*a*). PAFR activation alone did not reduce viral titers. Immunoblot analysis 48 hours after infection showed reduced RSV N and P protein abundance compared to untreated control cells (FIGS. 6*b,c*). These results demonstrate that PAFR activation enables viral load reduction by facilitating RNAi in airway epithelia.

Discussion

RNAi-based therapeutics have the potential to transform treatments for human diseases. However, there are a number of challenges that must be overcome. One is the efficient delivery to target organs. Local access to the respiratory tract is easily achieved, but barriers including the chemistry of synthetic siRNA oligos and the physical properties of the airways can impede successful delivery. Previous studies [15-17] and the present work illustrate the difficulty in silencing target genes with both naked and vehicle-formulated siRNAs. Cytoplasmic entry and retention of the oligonucleotides essential for further downstream RNAi effects have been shown to be problematic in this target tissue [15, 17].

Here, we show that PAFR engagement by its natural ligand or a structurally related LOS enhances peptide-mediated DsiRNA uptake and achieves target silencing. By manipulating this pathway for siRNA entry we decreased the abundance of endogenous transcripts and reduced the pathogenic load of an important respiratory virus. Consistent with this result, DsiRNA transfection following spiperone pretreatment also reduced mRNA transcript abundance.

Different endocytic pathways are used for the uptake of particles or soluble ligands. One mechanism, macropinocytosis, is achieved by plasma membrane ruffling [33]. Macropinocytosis is also a driving force for the entry of some bacteria and viruses [19, 34, 35]. Since it is non-selective, there is growing interest in co-opting macropinocytosis as a delivery mechanism for macromolecules and therapeutics. The peptide vehicle Transductin used in our DsiRNA formulations enters cells via macropinocytosis [36, 37]. We previously observed that Transductin facilitated DsiRNA entry and silencing of targets in well differentiated HAE when combined with enhancers of macropinocytosis such as EGF [17, 38] or phorbol esters (our unpublished data), but could not induce gene silencing when used alone. However, EGF treatment yielded very modest knockdown and phorbol ester, while associated with better silencing, is toxic and unsuitable for repeated applications or use in vivo [38]. Here, we exploited mechanisms that some respiratory pathogens use for entry. For example, pneumococcus and NTHi adhere to PAFR, which is coupled to the invasion of cells [18]. Additional studies showed that NTHi initiated cytoskeletal rearrangements in human airway epithelia resulting in bacterial internalization via macropinocytosis. Studies have also shown that PAF treatment induced endothelial actin cytoskeletal rearrangement [39]. Since cellular factors and activation signals are essential requirements for endocytosis, we hypothesized that activating PAFR signaling with known ligands might enhance siRNA internalization and silence target genes. Indeed, we found that PAFR engagement by LOS or PAF was essential for enhanced internalization and silencing of endogenous and exogenous targets.

PAFR is a G-protein coupled receptor that activates several signaling mechanisms after binding to its cognate receptors [40]. Upon binding, GTPase and phospholipases (C, D, and A2 pathways), protein kinase C (PKC) and tyrosine kinase signaling are activated. Similarly, in human bronchial epithelia, infection with NTHi 2019 increased $Ca^{2+}$ levels and cytosolic inositol phosphate levels [27] that were inhibited by a PAF antagonist [22]. Spiperone also enhances intracellular $Ca^{2+}$ through a protein-kinase and phospholipase C dependent pathway similar to PAFR activators [32], and when applied to HAE, enhanced silencing. To our knowledge spiperone is the only compound we tested that shares these properties with PAFR activators. Thus, the downstream effects of PAFR activation increase siRNA internalization in airway epithelia.

A potential limitation of this approach is that PAFR signaling also mediates inflammation. PAFR activation in cells and tissues may increase leukocyte trafficking and the generation of inflammatory responses [40-43]. Related to its induction of actin cytoskeletal rearrangements, PAF-mediated activation of endothelial cells induced vascular permeability and disassembly of interendothelial junctions [28]. F-actin and tight junction disruption has also been seen in intestinal epithelial cells [29]. We also observed that long-term PAF treatment (greater than 24 hours) reduced tight junction integrity. Although these responses are reversible by PAFR antagonists, such treatment may not be necessary as these exposures are longer than any intended in vitro or in vivo use. Alternatively, it may be possible to prepare synthetic NTHi LOS that binds PAFR but is non-inflammatory. For example pneumococcal interactions with PAF receptor fail to induce pro-inflammatory signaling cascades [23]. This ability of pneumococci to adhere to PAFR in the absence of signal transduction while retaining the ability to transcytose into cells suggests that uptake of siRNA delivery using this approach could be decoupled from inflammation.

In this work, we noted variability based on the lung donor. To improve on the very modest effects seen in some instances, repetitive dosing may be required. Nonetheless this work demonstrates for the first time that PAFR activation increases siRNA oligo delivery and provides a target pathway for further implementing the utility of RNAi to treat lung disease or prevent against lung pathogens.

Materials and Methods

Culture of Primary Epithelial Cells and Cell Lines.

Human airway epithelial cells were obtained from trachea and bronchi of lungs removed for organ donation from non-CF individuals. Cells were isolated by enzyme digestion as previously described [44]. Following enzymatic dispersion, cells were seeded at a density of $5\times10^5$ cells/cm$^2$ onto collagen-coated, 0.6 cm$^2$ semi permeable membrane filters (Millipore polycarbonate filters; Millipore Corp., Bedford, Mass.). The cells were maintained at 37° C. in a humidified atmosphere of 5% $CO_2$ air. Twenty-four hours after plating, the apical media was removed and the cells were maintained at an air-liquid interface (ALI) to allow differentiation of the epithelium. The culture medium consisted of 1:1 ratio mix of Dulbecco's modified Eagle's medium (DMEM)/Ham's F12, 5% Ultroser G (Biosepra S A, Cedex, France), 100 U/ml penicillin, 100 μg/ml streptomycin, 1% nonessential amino acids and 0.12 U/ml insulin. Studies were performed on well-differentiated epithelia approximately 4 to 6 weeks after initiation of the ALI cultures conditions. HEp-2 cells were maintained in MEM substituted with 10% fetal bovine serum and 100 U/ml penicillin.

DsiRNA Oligonucleotides.

All oligonucleotides employed in this study were synthesized using standard phosphoramidite chemistry, purified by RP-HPLC and used in sodium salt form IDT (Integrated DNA Technologies, Coralville, Iowa, USA). The predicted masses for the oligonucleotides were verified by electrospray-ionization mass spectrometry (ESI-MS) and were within +/−0.02%. The protocol for DsiRNA design and manufacture has been described in detail [45, 46]. The digoxigenin (DIG)-labeled DsiRNA was made by attaching DIG-NHS ester an internal-dT residue in a 2-O' methyl modified pig-HPRT-specific DsiRNA. The DsiRNAs used in this study are listed in Table 1.

TABLE 1

DsiRNA target and sequence

| DsiRNA | Target mRNA | Target sequence |
|---|---|---|
| hsHPRT | Human *HPRT* | 5' pGCCAGACUUUGUUGGAUUUGAAA**TT** (SEQ ID NO: 1)<br>3'UUCGGUCUGAAACAACCUAAACUUUAA (SEQ ID NO: 2) |
| **CFTR** | Human *CFTR* | 5' pGGAAGAAUUCUAUUCUCAAUCCA**AT** (SEQ ID NO: 3)<br>3'UUCCUUCUUAAGAUAAGAGUUAGGUUA (SEQ ID NO: 4) |
| **RSV N** | RSV *N* | 5' pGGAACAAGUUGUUGAGGUUUAUG**AA** (SEQ ID NO: 5)<br>3'UACCUUGUUCAACAACUCCAAAUACUU (SEQ ID NO: 6) |
| DIG-HPRT | Pig *HPRT* | 5' pCCAGUAAAGUUA*T*CACAUGUUUCUA**G** (SEQ ID NO: 7)<br>3'GUGGUCAUUUCAAUAGUGUACAAAGAUC (SEQ ID NO: 8) |
| NC1 | NegControl | 5' pCGUUAAUCGCGUAUAAUACGCGU**AT** (SEQ ID NO: 9)<br>3'CAGCAAUUAGCGCAUAUUAUGCGCAUA (SEQ ID NO: 10) |

DNA bases are in bold;
2'O methyl bases are underlined;
amino dT base coupled to DIG is in italics RNAi Transduction.

The PTD-DRBD peptide delivery reagent was purchased as Transductin from IDT. Transductin (Integrated DNA Technologies) was developed by Dr. Steven Dowdy at the UCSD School of Medicine [47]. It consists of a small fusion protein comprised of multiple Peptide Transduction Domains connected to a Double-Stranded RNA Binding Domain (PTD-DRBD). The fusion protein can be purified from bacteria expressing PTD-DRBD from a modified pTAT vector (available from Dr. Dowdy's lab). The detailed protocol for purification of the protein is available [47].

LOS Isolation.

LOS was isolated from NTHi strain 3198 or strain 2019htrB [48] or from *H. hemolyticus* (M19107) using the proteinase K-phenol water method previously described [49]. Bacteria were grown as a lawn for approximately 16 h on BHI medium plates with appropriate antibiotics at various temperatures at 37° C. in a $CO_2$ incubator overnight and were collected by flooding the plates with PBS and scraping colonies from the surfaces. Cells were centrifuged and suspended in a solution of 6 mM Tris base (Research Products International Corporation, Mt. Prospect, Ill.), 10 mM EDTA (Fisher Scientific, Fair Lawn, N.J.), and 2.0% (wt/vol) sodium dodecyl sulfate (SDS) (Research Products International), pH 6.8, containing 50 μg/ml proteinase K, were incubated at 65° C. for 1 h, and then were incubated overnight at 37° C. To remove SDS, samples were precipitated with 0.3 M sodium acetate and 3 volumes cold 100% ethanol, flash cooled in a dry ice-ethanol bath, and incubated overnight at −20° C. Samples were centrifuged for 10 min at 12,000×g at 4° C., and pellets were suspended in deionized water and precipitated a total of three times. Samples were suspended in water and treated with 80 U micrococcal nuclease (Sigma-Aldrich, St. Louis, Mo.) for 2 h at 37° C. LPS samples and phenol were equilibrated to 65° C., and an equal volume of phenol was added to the lysates. Samples were mixed, incubated at 65° C. for 30 min, cooled on ice, and centrifuged at 3,000 rpm for 10 min at 4° C. The aqueous layer was collected, and the organic layer was back extracted with an equal volume of water; aqueous layers were combined. Samples were precipitated with ethanol three times as described above to remove the phenol, and after the last precipitation pellets were suspended in high-performance liquid chromatography-grade water (Fisher Scientific) and lyophilized overnight in a VirTis (Gardiner, N.Y.) BenchTop 2K lyophilizer.

PAF and PAFRa.

PAF was purchased from Sigma-Aldrich. The reagent was reconstituted in ethanol and used in the experiment at a concentration of 200 nM or as described in the figures. PAF was added to the transfection mixture at the apical surface as well as to the basolateral media. PAFRa (WEB 2086) was purchased from Sigma-Aldrich. The reagent was reconstituted in DMSO and used at a concentration of 1 or 10 μM, added directly to the apical surface and the media 2 hours prior to transfection. The reagent was incubated with the cells throughout the transfection period.

Small Molecules.

All the small molecules tested were purchased from Sigma-Aldrich. The chemicals were reconstituted in appropriate solutions as recommended by the manufacturer. The epithelia were pre-treated with drugs for 6 hours at concentrations used in the CMAP study [30] or noted in the published literature. Following drug treatment, the epithelia were transduced with DsiRNA as described above.

Cytotoxicity Assay.

The LDH-cytotoxicity colorimetric assay kit (BioVision, Milpitas, Calif.) was used according to the manufacturer's instructions. Experimental and control samples were assayed in triplicate. The samples consisted of HAE cells treated with PAF and transfection with negative control DsiRNA or HPRT DsiRNA. A negative control consisted of culture medium from cells treated with DsiRNA but not PAF. The positive control medium came from cells exposed to Triton x-100 (1%) both apically and basolaterally for 30 minutes at 37° C. After the treatment period, 100 μl of culture media was transferred into an optically clear 96-well plate and an equal volume of reaction mixture added to each well and incubated for up to 30 minutes at room temperature. The absorbance was measured at 495 nm using a microplate reader (VERSAmax, Molecular Devices, Sunnyvale, Calif.). The background value was subtracted and the percentage cytotoxicity was calculated using the formula: (Test sample-Negative control)/(Positive control-Negative control)*100.

Transduction.

For well-differentiated airway epithelia, transfection was performed mostly according to the manufacturer's protocol. In all cases, the apical surface of epithelia was rinsed twice with PBS before adding the transfection mixture to the apical surface. DsiRNAs were used at a concentration of 250 nM. The mixture was left on the cells for 4 hours after which the medium was removed, the apical surface rinsed with PBS and the cells incubated further for 24 hours. For all experiments, a minimum of 3 biological replicates, in triplicate, were done.

RNA Isolation and Quantitative Reverse Transcription-q-PCR (RT-qPCR).

Total RNA was isolated using SV96 RNA isolation kit (Promega, Madison, Wis.), according to manufacturer's protocol. Total RNA (250 ng) were reverse transcribed using oligo (dT) (Roche Biochemicals, Indianapolis, Ind.) and random hexamers (Life Technologies, Carlsbad, Calif.) and Superscript II (Life Technologies, Carlsbad, Calif.) according to manufacturer's instructions. One-fifteenth of the cDNA was then amplified and analyzed by using the 5'-nuclease assay in a 7900 Real Time PCR System (Applied Biosystems, Foster city, CA) using primer-probe pairs reaction buffer and Immolase DNA polymerase (Bioline, Taunton, Mass.). The sequence of the primers and probes used in the reactions are detailed in Table 2. The reaction mix was contained in a total volume of 10 sl and the reaction condition was an initial cycle of 95° C. for 10 min, then 40 cycles of 95° C. for 15 s and 60° C. for 1 min. All data were normalized to the internal standard, RPL4 mRNA for pig airway samples and SFRS9 mRNA for human airway samples. Absolute quantification of an mRNA target sequence within an unknown sample was determined by reference to a standard curve. PCR efficiency for all reactions was within the acceptable margin of 90-110%. All results of the samples were presented as remaining target mRNA level in comparison to the mRNA level in the control samples (transduced with the NC1DsiRNA), which were normalized to 100%.

TABLE 2 qPCR primers and probes

| DsiRNA target | | Primer/Probe sequence |
|---|---|---|
| HPRT | Forward primer | GACTTTGCTTTCCTTGGTCAG (SEQ ID NO: 11) |
| | Reverse primer | GGCTTATATCCAACACTTCGTGGG (SEQ ID NO: 12) |
| | Probe | ATGGTCAAGGTCGCAAGCTTGCTGGT (SEQ ID NO: 13) |
| CFTR | Forward primer | CAACATCTAGTGAGCAGTCAGG (SEQ ID NO: 14) |
| | Reverse primer | CCCAGGTAAGGGATGTATTGTG (SEQ ID NO: 15) |
| | Probe | TCCAGATCCTGGAAATCAGGGTTAGT (SEQ ID NO: 16) |

TABLE 2-continued

| qPCR primers and probes | | |
|---|---|---|
| DsiRNA target | | Primer/Probe sequence |
| SFRS9 | Forward primer | TGTGCAGAAGGATGGAGT (SEQ ID NO: 17) |
| | Reverse primer | CTGGTGCTTCTCTCAGGGATA (SEQ ID NO: 18) |
| | Probe | TGGAATATGCCCTGCGTAAACTGGA (SEQ ID NO: 19) |

Connectivity Map Analysis.

The connectivity map (CMAP) is a public database of human cell line gene expression data sets representing responses to drug treatments that can be queried using input gene expression signatures to identify small molecules that share similar gene expression patterns [30]. We used input query signatures derived from published microarray data of gene expression changes associated with stimulation of PAFR [31]. Specifically, genes with more than 3-fold expression change from 0 to 4 days culture or 0 to 8 days were used as input signatures (probe ID defined by the Affymetrix GeneChip Human Genome U133A array). Each reference signature in the database was compared with the input signature and given a score termed the "connectivity score" based on the extent of similarity between the two. Scores ranged from +1 (+ correlation), 0 (no correlation) and −1 (reverse correlation). We selected candidate agents with connectivity scores approximating +1.

RSV.

For infections, RSV aliquots were resuspended in cold DMEM or DMEM/F12. RSV strain A2 (wt RSV) was kindly provided by Barney Graham (NIH, Bethesda, Md.), and working stocks of RSV were prepared in HEp-2 cells (ATCC).

RSV Infection:

RSV infection of HAE for both for immunoblot and viral titer was done at an MOI of 1. The virus was thawed at 37° C. and diluted in MEM (0% FCS) to a volume of 70 μl (1MOI)/well. The cells in Millicell filters were rinsed with the same media once and the virus applied to the apical surface. The plate was incubated at 37° C. for a period of 2 hours. After the incubation period, the virus inoculum was rinsed with MEM three times to remove any traces of the virus. The plates were then incubated at 37° C. until used for the assay.

Plaque Assay for Assessing RSV Titer in Cell Supernatant.

HEp-2 cells were seeded onto 12-well plate at a sufficient density so that it reached 90-95% confluence the next day. RSV stock was serially diluted in a 96-well u-bottom plate in serum-free MEM. 200 μl of this dilution was added to the wells of the HEp-2 cells and allowed to incubate at 37° C. for 2 hours. At the end of the incubation period, the inoculum was removed and the cells were overlayed with 2 ml of a 1:1 mixture of complete EMEM and 1% agarose (SeaKem ME agarose, Lonza). The plates were allowed to incubate for 5 days at 37° C. After this period, the cells were stained with a second overlay (1 ml) with a similar mixture as first, but with the addition of 0.015% neutral red. The cells were incubated for an additional 24 hours at 37° C. after which the plaques were counted under a light box. The viral titer were then estimated as plaque forming units per ml (PFU/ml) and plotted as $\log_{10}$ PFU/ml.

Immunoblotting.

HAE were rinsed with PBS and lysed in RIPA buffer (1% NP-40, 0.5% sodium deoxycholate, 0.1% SDS, 50 mM Tris, protease inhibitors [complete; mini, EDTA-free; Roche Biochemicals, Indianapolis, Ind.]) for 30 minutes at 4° C. The lysate were centrifuged in a table top centrifuge at 14,000 rpm for 20 minutes at 4° C. The supernatant was quantified by BCA protein assay kit (Pierce, Rockford, Ill.). Thirty micrograms of protein per lane was separated on a 10% Tris-HCL Criterion precast gel (Bio-Rad, Hercules, Calif.) for western blot analysis. The protein was transferred to Polyvinylidene difluoride membrane and then was probed with goat anti-RSV antibody purchased from Meridian Life Sciences (Memphis, Tenn.). The membrane was imaged, and then stripped with Restore Western Blot Stripping Buffer (Thermo Scientific, Lafayette, Colo.) for 15 minutes. The membrane was rinsed with Tris-buffered saline-Tween (TBS-T) and blocked in 5% bovine serum albumin (Research Products International Corp, Mt. Prospect, Ill.). The membrane was then reprobed with α-tubulin (Sigma-Aldrich).

Confocal Imaging.

The primary human airway epithelia grown at the air-liquid interface were transfected with the DIG-labeled DsiRNA at a concentration of 250 nM after complexing with Transductin. The transfection mixture was left on the apical surface for 1 h. At the end of this period, the cells were fixed in 2% formaldehyde, permeabilized in 0.2% Triton-x-100 and blocked in 1% BSA for 1 h. The cells were then stained with mouse antibody to DIG (Roche Biochemicals, Indianapolis, Ind.) for 1 h, followed by Alexa 488 labeled goat anti-mouse secondary antibody for 1 h, and then Alexa 488 labeled rabbit anti-mouse tertiary antibody (Life Technologies, Carlsbad, Calif.). In some cases an Alexa 564 goat anti-mouse secondary antibody was used. The cells were finally stained with nuclear stain, ToPro 3 for 10 minutes. The filter, containing the cells, was removed from the culture insert by cutting the edges with razor blade, and mounted on a slide with Vectashield (Vector Laboratories Inc, Burlingame, Calif.). The cells were visualized by confocal microscopy (Bio-Rad Radience 2100MP Multiphoton/Confocal Microscope, Bio-Rad, Hercules, Calif.).

Statistical Analyses.

The data from quantitative experiments were analyzed using paired Student's t-test analysis or repeated measures ANOVA as appropriate. All of the data presented are representative of the results of at least three or more independent experiments.

REFERENCES

1. Sanders, N, Rudolph, C, Braeckmans, K, De Smedt, S C, and Demeester, J (2009). Extracellular barriers in respiratory gene therapy. *Adv Drug Deliv Rev* 61: 115-127.
2. Zuhorn, I S, Engberts, J B, and Hoekstra, D (2007). Gene delivery by cationic lipid vectors: overcoming cellular barriers. *Eur Biophys J* 36: 349-362.
3. Alvarez, R, Elbashir, S, Borland, T, Toudjarska, I, Hadwiger, P, John, M, et al. (2009). RNA interference-mediated silencing of the respiratory syncytial virus nucleocapsid defines a potent antiviral strategy. *Antimicrob Agents Chemother* 53: 3952-3962.
4. Bitko, V, Musiyenko, A, Shulyayeva, O, and Barik, S (2005). Inhibition of respiratory viruses by nasally administered siRNA. *Nat Med* 11: 50-55.

5. DeVincenzo, J, Lambkin-Williams, R, Wilkinson, T, Cehelsky, J, Nochur, S, Walsh, E, et al. (2010). A randomized, double-blind, placebo-controlled study of an RNAi-based therapy directed against respiratory syncytial virus. *Proceedings of the National Academy of Sciences of the United States of America* 107: 8800-8805.

6. Kim, T H, Kim, S H, Seo, J Y, Chung, H, Kwak, H J, Lee, S K, et al. (2011). Blockade of the Wnt/beta-catenin pathway attenuates bleomycin-induced pulmonary fibrosis. *Tohoku J Exp Med* 223: 45-54.

7. Lomas-Neira, J L, Chung, C S, Wesche, D E, Peri, M, and Ayala, A (2005). In vivo gene silencing (with siRNA) of pulmonary expression of MIP-2 versus KC results in divergent effects on hemorrhage-induced, neutrophil-mediated septic acute lung injury. *J Leukoc Biol* 77: 846-853.

8. Merkel, O M, Zheng, M, Debus, H, and Kissel, T (2012). Pulmonary gene delivery using polymeric nonviral vectors. *Bioconjug Chem* 23: 3-20.

9. Perl, M, Chung, C S, Lomas-Neira, J, Rachel, T M, Biffl, W L, Cioffi, W G, et al. (2005). Silencing of Fas, but not caspase-8, in lung epithelial cells ameliorates pulmonary apoptosis, inflammation, and neutrophil influx after hemorrhagic shock and sepsis. *Am J Pathol* 167: 1545-1559.

10. Rosas-Taraco, A G, Higgins, D M, Sanchez-Campillo, J, Lee, E J, Orme, I M, and Gonzalez-Juarrero, M (2009). Intrapulmonary delivery of XCL1-targeting small interfering RNA in mice chronically infected with *Mycobacterium tuberculosis*. *Am J Respir Cell Mol Biol* 41: 136-145.

11. Senoo, T, Hattori, N, Tanimoto, T, Furonaka, M, Ishikawa, N, Fujitaka, K, et al. (2010). Suppression of plasminogen activator inhibitor-1 by RNA interference attenuates pulmonary fibrosis. *Thorax* 65: 334-340.

12. Zhang, X, Shan, P, Jiang, D, Noble, P W, Abraham, N G, Kappas, A, et al. (2004). Small interfering RNA targeting heme oxygenase-1 enhances ischemia-reperfusion-induced lung apoptosis. *The Journal of biological chemistry* 279: 10677-10684.

13. Ge, Q, Filip, L, Bai, A, Nguyen, T, Eisen, H N, and Chen, J (2004). Inhibition of influenza virus production in virus-infected mice by RNA interference. *Proceedings of the National Academy of Sciences of the United States of America* 101: 8676-8681.

14. Robbins, M, Judge, A, Ambegia, E, Choi, C, Yaworski, E, Palmer, L, et al. (2008). Misinterpreting the therapeutic effects of small interfering RNA caused by immune stimulation. *Hum Gene Ther* 19: 991-999.

15. Moschos, S A, Frick, M, Taylor, B, Turnpenny, P, Graves, H, Spink, K G, et al. (2011). Uptake, efficacy, and systemic distribution of naked, inhaled short interfering RNA (siRNA) and locked nucleic acid (LNA) antisense. *Mol Ther* 19: 2163-2168.

16. Platz, J, Pinkenburg, O, Beisswenger, C, Puchner, A, Damm, T, and Bals, R (2005). Application of small interfering RNA (siRNA) for modulation of airway epithelial gene expression. *Oligonucleotides* 15: 132-138.

17. Krishnamurthy, S, Behlke, M A, Ramachandran, S, Salem, A K, McCray, P B, Jr., and Davidson, B L (2012). Manipulation of Cell Physiology Enables Gene Silencing in Well-differentiated Airway Epithelia. *Mol Ther Nucleic Acids* 1: e41.

18. Ketterer, M R, Shao, J Q, Hornick, D B, Buscher, B, Bandi, V K, and Apicella, M A (1999). Infection of primary human bronchial epithelial cells by *Haemophilus influenzae*: macropinocytosis as a mechanism of airway epithelial cell entry. *Infection and immunity* 67: 4161-4170.

19. Mercer, J, and Helenius, A (2009). Virus entry by macropinocytosis. *Nat Cell Biol* 11: 510-520.

20. Moniot, B, Declosmenil, F, Barrionuevo, F, Scherer, G, Aritake, K, Malki, S, et al. (2009). The PGD2 pathway, independently of FGF9, amplifies SOX9 activity in Sertoli cells during male sexual differentiation. *Development* 136: 1813-1821.

21. Robbins, M L, Sekhon, R S, Meeley, R, and Chopra, S (2008). A Mutator transposon insertion is associated with ectopic expression of a tandemly repeated multicopy Myb gene pericarp colorl of maize. *Genetics* 178: 1859-1874.

22. Swords, W E, Buscher, B A, Ver Steeg Ii, K, Preston, A, Nichols, W A, Weiser, J N, et al. (2000). Non-typeable *Haemophilus influenzae* adhere to and invade human bronchial epithelial cells via an interaction of lipooligosaccharide with the PAF receptor. *Mol Microbiol* 37: 13-27.

23. Cundell, D R, Gerard, N P, Gerard, C, Idanpaan-Heikkila, I, and Tuomanen, E I (1995). *Streptococcus pneumoniae* anchor to activated human cells by the receptor for platelet-activating factor. *Nature* 377: 435-438.

24. Zhang, J R, Mostov, K E, Lamm, M E, Nanno, M, Shimida, S, Ohwaki, M, et al. (2000). The polymeric immunoglobulin receptor translocates pneumococci across human nasopharyngeal epithelial cells. *Cell* 102: 827-837.

25. Pezzulo, A A, Starner, T D, Scheetz, T E, Traver, G L, Tilley, A E, Harvey, B G, et al. (2011). The air-liquid interface and use of primary cell cultures are important to recapitulate the transcriptional profile of in vivo airway epithelia. *Am J Physiol Lung Cell Mol Physiol* 300: L25-31.

26. Preston, A, Mandrell, R E, Gibson, B W, and Apicella, M A (1996). The lipooligosaccharides of pathogenic gram-negative bacteria. *Crit Rev Microbiol* 22: 139-180.

27. Shukla, S D (1992). Platelet-activating factor receptor and signal transduction mechanisms. *FASEB J* 6: 2296-2301.

28. Knezevic, I I, Predescu, S A, Neamu, R F, Gorovoy, M S, Knezevic, N M, Easington, C, et al. (2009). Tiam1 and Rac1 are required for platelet-activating factor-induced endothelial junctional disassembly and increase in vascular permeability. *The Journal of biological chemistry* 284: 5381-5394.

29. Xu, L F, Xu, C, Mao, Z Q, Teng, X, Ma, L, and Sun, M (2011). Disruption of the F-actin cytoskeleton and monolayer barrier integrity induced by PAF and the protective effect of ITF on intestinal epithelium. *Arch Pharm Res* 34: 245-251.

30. Lamb, J, Crawford, E D, Peck, D, Modell, J W, Blat, I C, Wrobel, M J, et al. (2006). The Connectivity Map: using gene-expression signatures to connect small molecules, genes, and disease. *Science* 313: 1929-1935.

31. Travers, J B, Edenberg, H J, Zhang, Q, Al-Hassani, M, Yi, Q, Baskaran, S, et al. (2008). Augmentation of UVB radiation-mediated early gene expression by the epidermal platelet-activating factor receptor. *J Invest Dermatol* 128: 455-460.

32. Liang, L, MacDonald, K, Schwiebert, E M, Zeitlin, P L, and Guggino, W B (2009). Spiperone, identified through compound screening, activates calcium-dependent chloride secretion in the airway. *Am J Physiol Cell Physiol* 296: C131-141.

33. Watts, C, and Marsh, M (1992). Endocytosis: what goes in and how? *J Cell Sci* 103 (Pt 1): 1-8.

34. Francis, C L, Ryan, T A, Jones, B D, Smith, S J, and Falkow, S (1993). Ruffles induced by *Salmonella* and other stimuli direct macropinocytosis of bacteria. *Nature* 364: 639-642.

35. Watarai, M, Derre, I, Kirby, J, Growney, J D, Dietrich, W F, and Isberg, R R (2001). *Legionella pneumophila* is internalized by a macropinocytotic uptake pathway controlled by the Dot/Icm system and the mouse Lgn1 locus. *J Exp Med* 194: 1081-1096.

36. Imamura, J, Suzuki, Y, Gonda, K, Roy, C N, Gatanaga, H, Ohuchi, N, et al. (2011). Single particle tracking confirms that multivalent Tat protein transduction domain-induced heparan sulfate proteoglycan cross-linkage activates Rac1 for internalization. The *Journal of biological chemistry* 286: 10581-10592.

37. Kaplan, I M, Wadia, J S, and Dowdy, S F (2005). Cationic TAT peptide transduction domain enters cells by macropinocytosis. *J Control Release* 102: 247-253.

38. Goel, G, Makkar, H P, Francis, G, and Becker, K (2007). Phorbol esters: structure, biological activity, and toxicity in animals. *Int J Toxicol* 26: 279-288.

39. Bussolino, F, Camussi, G, Aglietta, M, Braquet, P, Bosia, A, Pescarmona, G, et al. (1987). Human endothelial cells are target for platelet-activating factor. I. Platelet-activating factor induces changes in cytoskeleton structures. *J Immunol* 139: 2439-2446.

40. Chao, W, and Olson, M S (1993). Platelet-activating factor: receptors and signal transduction. *Biochem J* 292 (Pt 3): 617-629.

41. Henson, P M, Barnes, P J, and Banks-Schlegel, S P (1992). NHLBI workshop summary. Platelet-activating factor: role in pulmonary injury and dysfunction and blood abnormalities. *Am Rev Respir Dis* 145: 726-731.

42. Shirasaki, H, Nishikawa, M, Adcock, I M, Mak, J C, Sakamoto, T, Shimizu, T, et al. (1994). Expression of platelet-activating factor receptor mRNA in human and guinea pig lung. *Am J Respir Cell Mol Biol* 10: 533-537.

43. Stoll, L L, Denning, G M, Kasner, N A, and Hunninghake, G W (1994). Platelet-activating factor may stimulate both receptor-dependent and receptor-independent increases in [Ca2+] in human airway epithelial cells. *The Journal of biological chemistry* 269: 4254-4259.

44. Yamaya, M, Finkbeiner, W E, Chun, S Y, and Widdicombe, J H (1992). Differentiated structure and function of cultures from human tracheal epithelium. *Am J Physiol* 262: L713-724.

45. Amarzguioui, M, Lundberg, P, Cantin, E, Hagstrom, J, Behlke, M A, and Rossi, J J (2006). Rational design and in vitro and in vivo delivery of Dicer substrate siRNA. *Nat Protoc* 1: 508-517.

46. Collingwood, M A, Rose, S D, Huang, L, Hillier, C, Amarzguioui, M, Wiiger, M T, et al. (2008). Chemical modification patterns compatible with high potency dicer-substrate small interfering RNAs. *Oligonucleotides* 18: 187-200.

47. Eguchi, A, Meade, B R, Chang, Y C, Fredrickson, C T, Willert, K, Puri, N, et al. (2009). Efficient siRNA delivery into primary cells by a peptide transduction domain-dsRNA binding domain fusion protein. *Nat Biotechnol* 27: 567-571.

48. Lee, N G, Sunshine, M G, Engstrom, J J, Gibson, B W, and Apicella, M A (1995). Mutation of the htrB locus of *Haemophilus influenzae* nontypable strain 2019 is associated with modifications of lipid A and phosphorylation of the lipo-oligosaccharide. *The Journal of biological chemistry* 270: 27151-27159.

49. McLendon, M K, Schilling, B, Hunt, J R, Apicella, M A, and Gibson, B W (2007). Identification of LpxL, a late acyltransferase of *Francisella tularensis. Infection and immunity* 75: 5518-5531.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of reducing a level of a target mRNA in a well-differentiated airway epithelial cell comprising contacting the cell with a therapeutic RNAi agent and a composition comprising a Platelet-activating factor receptor (PAFR) ligand, wherein the mRNA level of the target mRNA is reduced by at least 1% as compared to a control cell that has not been contacted with PAFR, wherein the PAFR is Platelet-activating factor (PAF), lipooligosaccharide (LOS), spiperone and/or teichoic acid, wherein the therapeutic RNAi agent is a Dicer-substrate RNA (DsiRNA) molecule comprising SEQ ID NO: 1 and SEQ ID NO: 2 (hsHPRT); SEQ ID NO: 3 and SEQ ID NO: 4 (CFTR); SEQ ID NO: 5 and SEQ ID NO: 6 (RSV N); or SEQ ID NO: 7 and SEQ ID NO: 8 (DIG-HPRT).

2. The method of claim 1, wherein well-differentiated cell is more than five days old.

3. The method of claim 1, wherein the airway epithelial cell is a lung cell, a nasal cell, a tracheal cell, a bronchial cell, a bronchiolar or alveolar epithelial cell.

4. The method of claim 1, wherein the airway epithelial cells are present in a mammal.

5. The method of claim 1, wherein the airway epithelial cell is a CF epithelial cell.

6. The method of claim 1, wherein the therapeutic RNAi agent and the composition is administered orally or by inhalation.

7. The method of claim 1, wherein the PAFR ligand is present within a pharmaceutical composition.

8. A method of treating a subject having an airway epithelial disease comprising administering to the subject an effective amount of a therapeutic agent and a composition comprising a Platelet-activating factor receptor (PAFR) ligand to alleviate the symptoms of the airway epithelial disease by inducing a therapeutic effect, wherein the symptoms are reduced by at least 1%, wherein the therapeutic agent comprises Aminoglutethimide, Biperiden, Diphenhydramine, Rottlerin, Midodrine, Thioridazine, Sulfadimethoxine, neostigmine bromide, Pyridostigmine, pizotifen, tyrophostin (AG-1478), valproic acid, Scriptaid, neomycin, or an RNAi agent that is a Dicer-substrate RNA (DsiRNA) molecule comprising SEQ ID NO: 1 and SEQ ID NO: 2 (hsHPRT); SEQ ID NO: 3 and SEQ ID NO: 4 (CFTR); SEQ ID NO: 5 and SEQ ID NO: 6 (RSV N); or SEQ ID NO: 7 and SEQ ID NO: 8 (DIG-HPRT).

9. The method of claim 8, wherein the PAFR is Platelet-activating factor (PAF), lipooligosaccharide (LOS), spiperone and/or teichoic acid.

10. The method of claim 8, wherein the therapeutic RNAi agent and the composition is administered orally or by inhalation.

11. The method of claim 8, wherein the therapeutic RNAi agent and the composition is administered by aerosol, dry powder, bronchoscopic instillation, or intra-airway (tracheal or bronchial) aerosol and the therapeutic agent is administered orally, by inhalation, by aerosol, dry powder, bronchoscopic instillation, or intra-airway (tracheal or bronchial) aerosol.

12. The method of claim 8, wherein the therapeutic agent is present within a pharmaceutical composition.

13. The method of claim 8, wherein the airway epithelial disease is cystic fibrosis.

* * * * *

SEQUENCE LISTING

```
<160> NUMBER OF SEQ ID NOS: 19

<210> SEQ ID NO 1
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1

gccagacuuu guuggauuug aaatt                                           25


<210> SEQ ID NO 2
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2

aauuucaaau ccaacaaagu cuggcuu                                         27


<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3

ggaagaauuc uauucucaau ccaat                                           25


<210> SEQ ID NO 4
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4

auuggauuga gaauagaauu cuuccuu                                         27


<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5

ggaacaaguu guugagguuu augaa                                           25


<210> SEQ ID NO 6
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6

uucauaaacc ucaacaacuu guuccau                                         27
```

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 7
ccaguaaagu uatcacaugu uucuag 26

<210> SEQ ID NO 8
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 8
cuagaaacau gugauaacuu uacuggug 28

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 9
cguuaaucgc guauaauacg cguat 25

<210> SEQ ID NO 10
<211> LENGTH: 27
<212> TYPE: RNA
<213> ORGANISM: Artificial Sequence
<220> FEATURE:
<223> OTHER INFORMATION: Description of Artificial Sequence: Synthetic primer

<400> SEQUENCE: 10
auacgcguau uauacgcgau uaacgac 27

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gactttgctt tccttggtca g 21

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
ggcttatatc caacacttcg tggg 24

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 13
atggtcaagg tcgcaagctt gctggt 26

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
caacatctag tgagcagtca gg 22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
cccaggtaag ggatgtattg tg 22

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 16
tccagatcct ggaaatcagg gttagt 26

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
tgtgcagaag gatggagt 18

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic primer -continued

```
<400> SEQUENCE: 18

ctggtgcttc tctcagggat a                                               21


<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19

tggaatatgc cctgcgtaaa ctgga                                           25
```